United States Patent
Martinez-Enriquez et al.

(10) Patent No.: US 11,382,505 B2
(45) Date of Patent: Jul. 12, 2022

(54) METHOD OF ESTIMATING A FULL SHAPE OF THE CRYSTALLINE LENS FROM MEASUREMENTS TAKEN BY OPTIC IMAGING TECHNIQUES AND METHOD OF ESTIMATING AN INTRAOCULAR LENS POSITION IN A CATARACT SURGERY

(71) Applicant: CONSEJO SUPERIOR DE INVESTIGACIONES CIENTIFICAS, Madrid (ES)

(72) Inventors: Eduardo Martinez-Enriquez, Madrid (ES); Susana Marcos-Celestino, Madrid (ES); Carlos Dorronsoro-Diaz, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 112 days.

(21) Appl. No.: 16/870,592

(22) Filed: May 8, 2020

(65) Prior Publication Data
US 2020/0268248 A1 Aug. 27, 2020

Related U.S. Application Data

(63) Continuation-in-part of application No. 15/583,441, filed on May 1, 2017, now Pat. No. 10,810,756.
(Continued)

(51) Int. Cl.
*A61B 3/117* (2006.01)
*G06T 7/62* (2017.01)
(Continued)

(52) U.S. Cl.
CPC .......... *A61B 3/1173* (2013.01); *A61B 3/0025* (2013.01); *A61B 3/102* (2013.01);
(Continued)

(58) Field of Classification Search
CPC ..... A61B 3/0025; A61B 3/102; A61B 3/1173; G06T 7/344; G06T 7/50; G06T 7/62;
(Continued)

(56) References Cited

U.S. PATENT DOCUMENTS 8,321,184 B1 * 11/2012 Urs ...................... A61F 2/1613
703/2
2001/0024265 A1 * 9/2001 Fujieda ................ A61B 3/1005
351/208
(Continued)

OTHER PUBLICATIONS

Martinez-Enriquez et al. "Optical coherence tomography based estimates of crystalline lens volume, equatorial diameter, and plane position." Investigative ophthalmology & visual science 57.9 (2016): OCT600-OCT610. (Year: 2016).*
(Continued)

*Primary Examiner* — Katrina R Fujita

(57) ABSTRACT

The present invention relates to a method and a device for estimating a full shape of a lens of an eye from measurements of the lens taken in-vivo by optical imaging techniques, the measurements comprising visible portions of the lens, the method comprises defining non-visible portions of the lens parting from the in-vivo measurements and using a geometrical model of a lens previously built from ex-vivo measurements. The full shape parameters of the crystalline lens can be estimated in the present invention from optical imaging techniques to improve the estimation of the IOL position and thus the IOL power selection.

18 Claims, 14 Drawing Sheets

Related U.S. Application Data

(60) Provisional application No. 62/329,392, filed on Apr. 29, 2016.

(51) Int. Cl.
*G06T 7/50* (2017.01)
*A61B 3/00* (2006.01)
*A61B 3/10* (2006.01)
*G06T 7/70* (2017.01)

(52) U.S. Cl.
CPC ............... *G06T 7/50* (2017.01); *G06T 7/62* (2017.01); *G06T 7/70* (2017.01); *G06T 2207/10101* (2013.01); *G06T 2207/30041* (2013.01)

(58) Field of Classification Search
CPC ............. G06T 7/70; G06T 2207/10101; G06T 2207/30041
See application file for complete search history.

(56) References Cited

U.S. PATENT DOCUMENTS

| | | | | |
|---|---|---|---|---|
| 2007/0052925 | A1* | 3/2007 | Barth | G01B 11/14 351/211 |
| 2010/0121612 | A1* | 5/2010 | Ho | A61F 2/16 703/1 |
| 2012/0155726 | A1* | 6/2012 | Li | G06T 7/0014 382/128 |
| 2017/0079526 | A1* | 3/2017 | Tamura | A61B 3/09 |
| 2020/0311925 | A1* | 10/2020 | Shiba | A61B 3/145 |

OTHER PUBLICATIONS

Martinez-Enriquez et al. "OCT-based full crystalline lens shape change during accommodation in vivo." Biomedical optics express 8.2 (2017): 918-933. (Year: 2017).*

Navarro et al. "Adaptive model of the gradient index of the human lens. I. Formulation and model of aging ex vivo lenses." Josa A 24.8 (2007): 2175-2185. (Year: 2007).*

Navarro et al. "Adaptive model of the gradient index of the human lens. II. Optics of the accommodating aging lens." Josa A 24.9 (2007): 2911-2920. (Year: 2007).*

Ortiz et al. "Optical distortion correction in optical coherence tomography for quantitative ocular anterior segment by three-dimensional imaging." Optics express 18.3 (2010): 2782-2796. (Year: 2010).*

Urs et al. "Shape of the isolated ex-vivo human crystalline lens." Vision research 49.1 (2009): 74-83. (Year: 2009).*

Urs et al. "Age-dependent Fourier model of the shape of the isolated ex vivo human crystalline lens." Vision research 50.11 (2010): 1041-1047. (Year: 2010).*

* cited by examiner

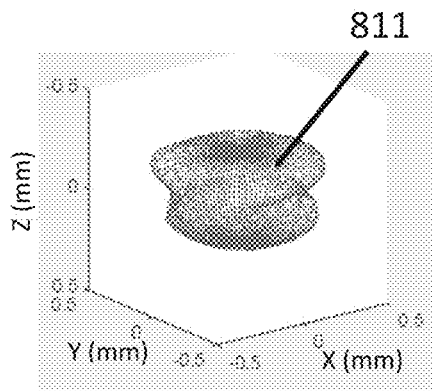
FIG. 5A1
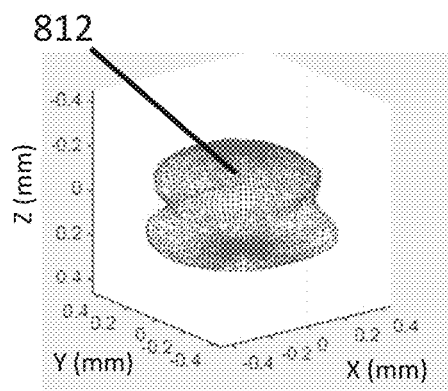
FIG. 5A2
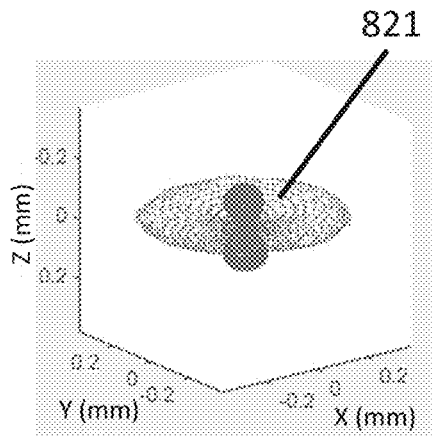
FIG. 5B1
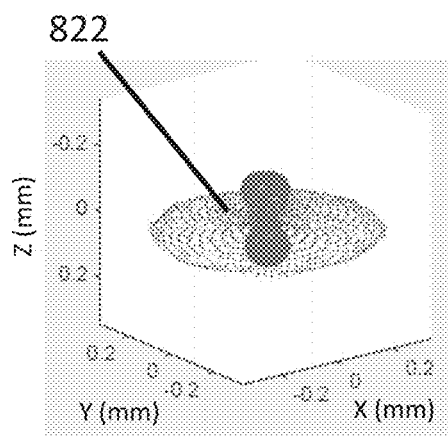
FIG. 5B2
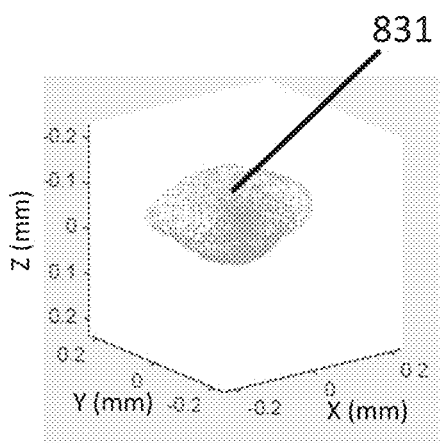
FIG. 5C1
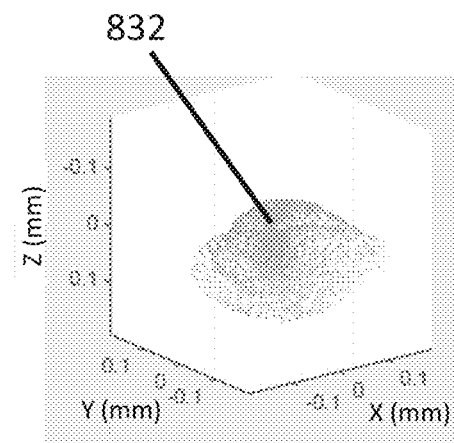
FIG. 5C2

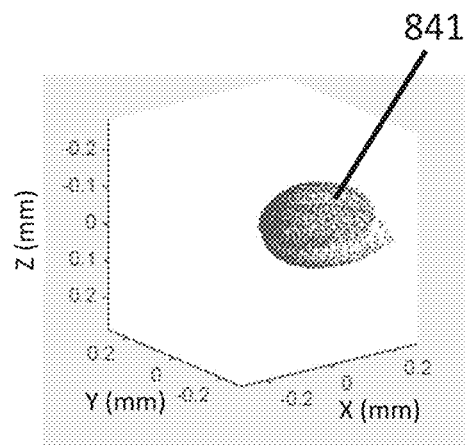
FIG. 5D1
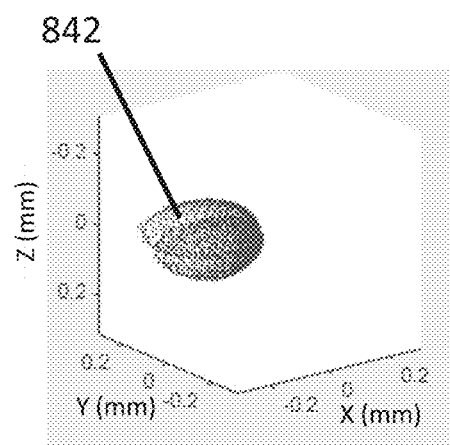
FIG. 5D2
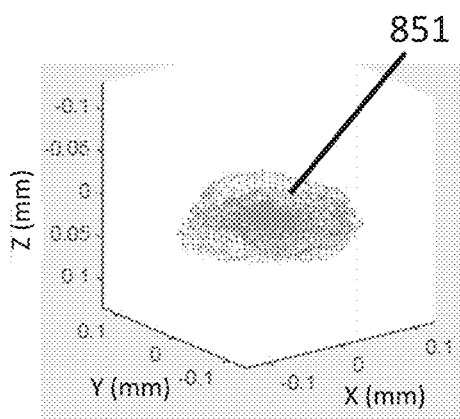
FIG. 5E1
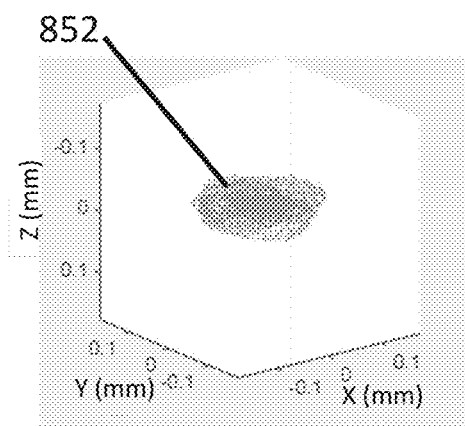
FIG. 5E2

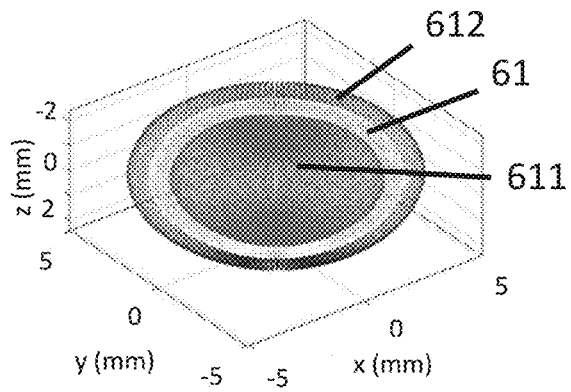
FIG. 6A1
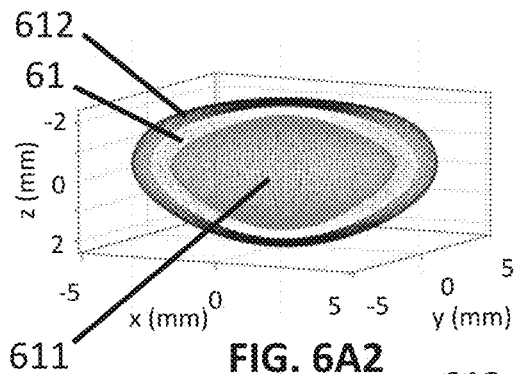
FIG. 6A2
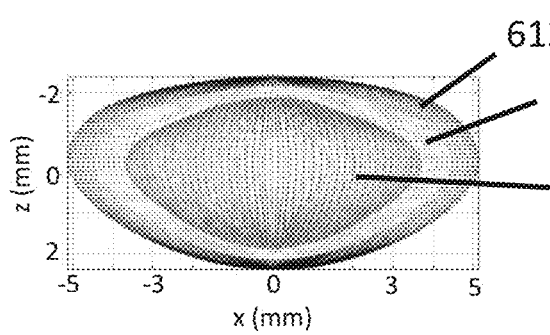
FIG. 6A3
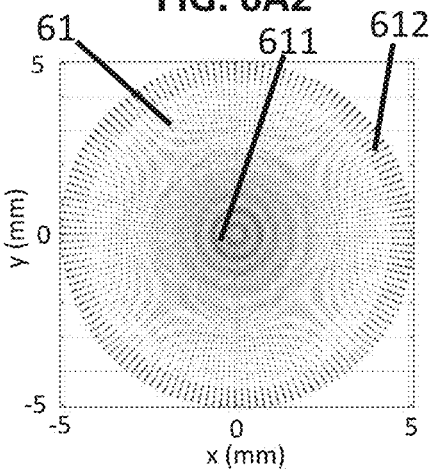
FIG. 6A4
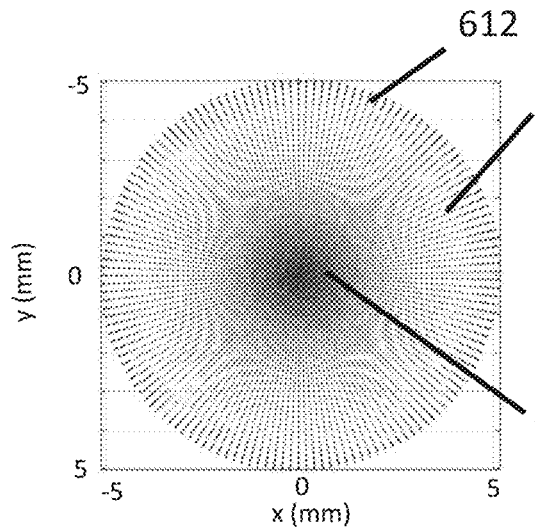
FIG. 6A5
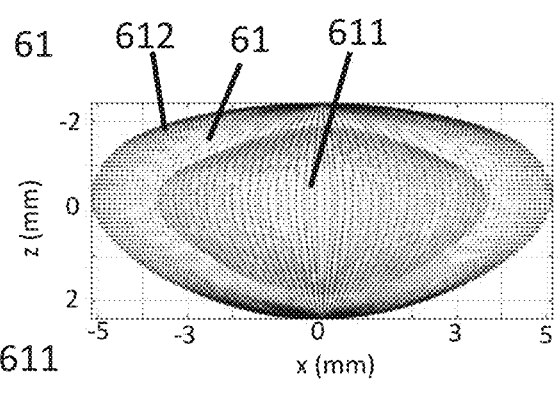
FIG. 6A6

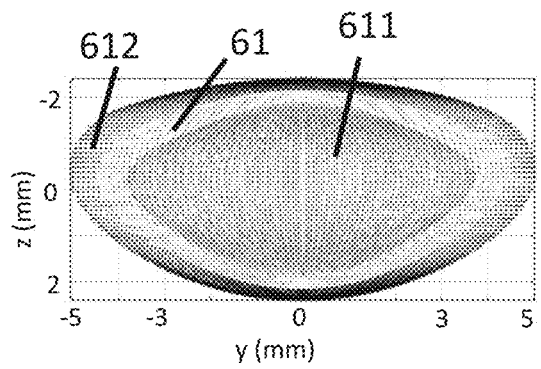
FIG. 6A7
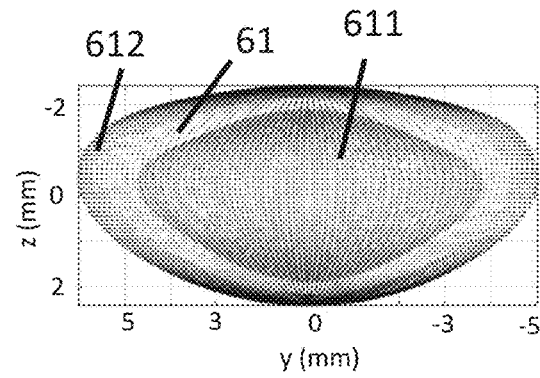
FIG. 6A8
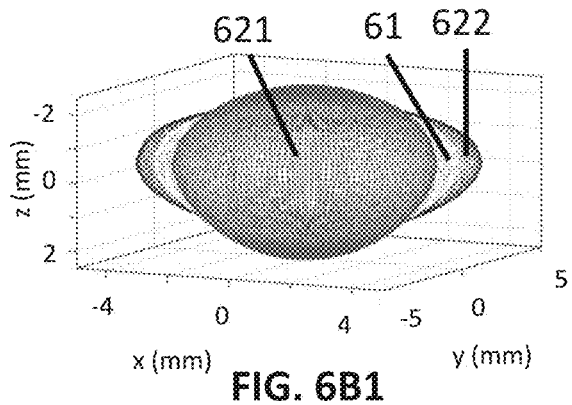
FIG. 6B1
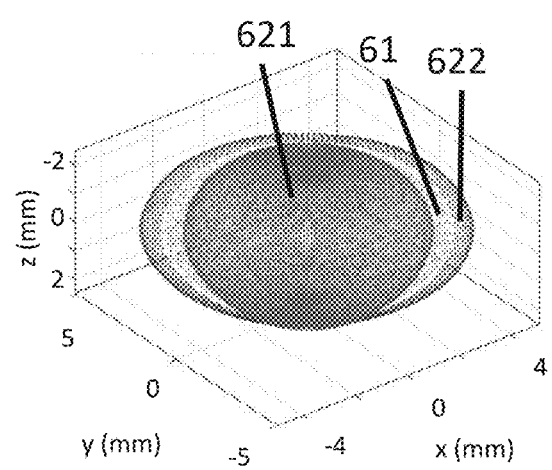
FIG. 6B2
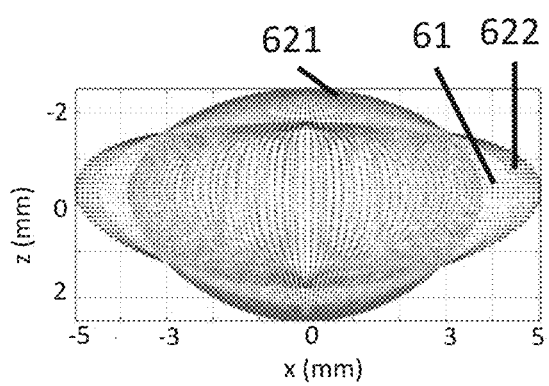
FIG. 6B3
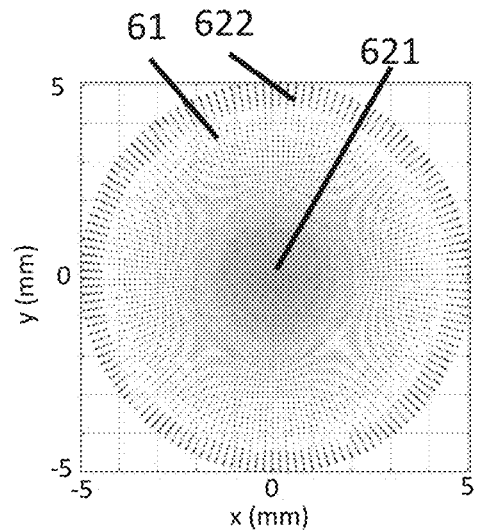
FIG. 6B4

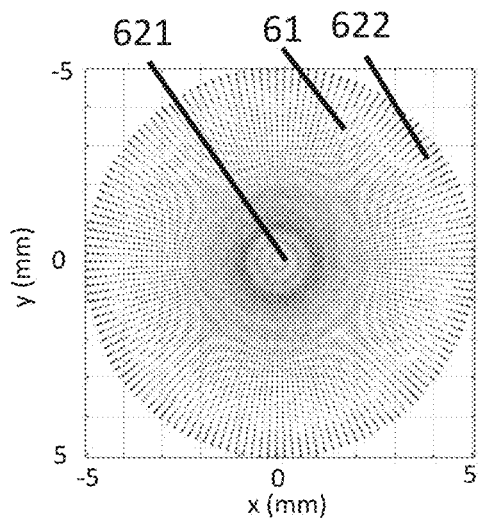
FIG. 6B5
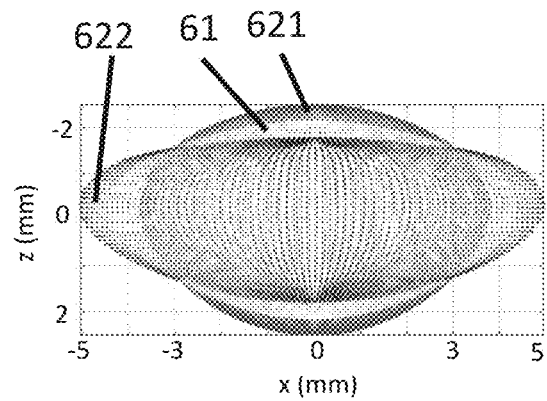
FIG. 6B6
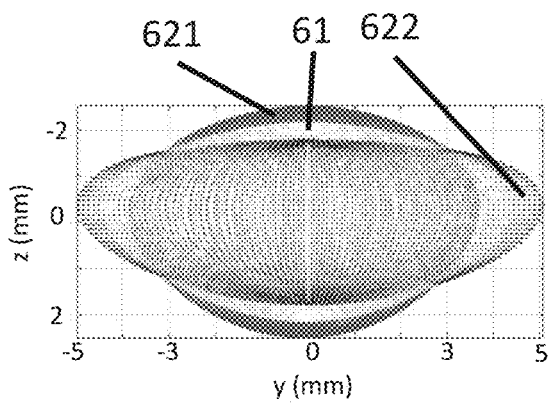
FIG. 6B7
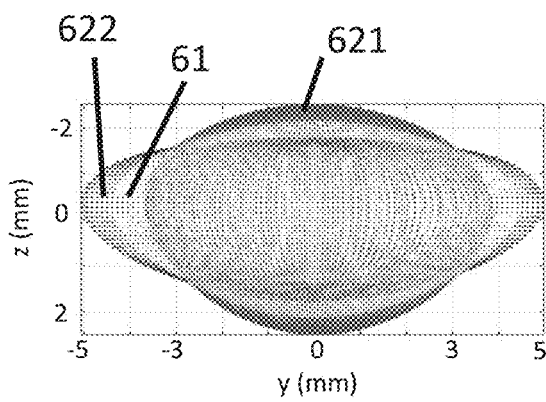
FIG. 6B8
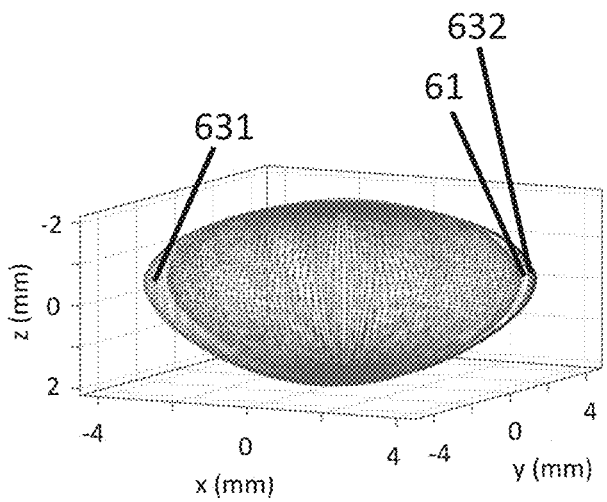
FIG. 6C1
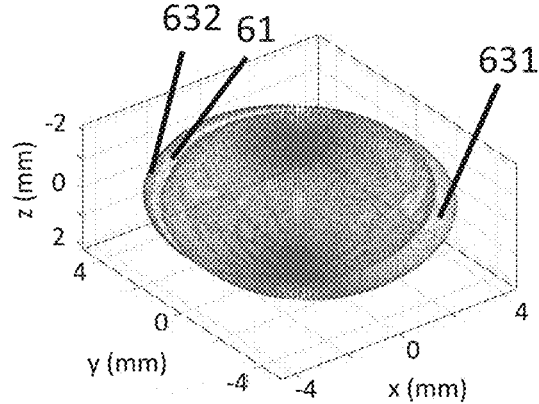
FIG. 6C2

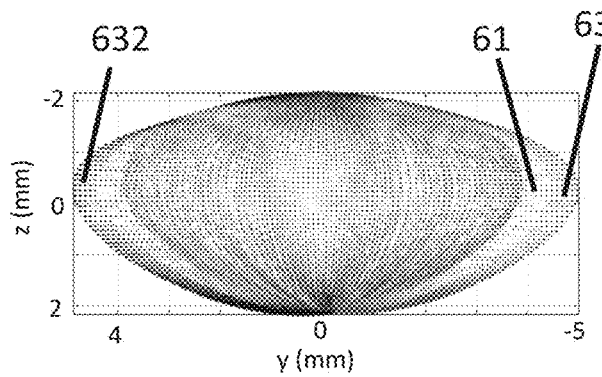
FIG. 6C3
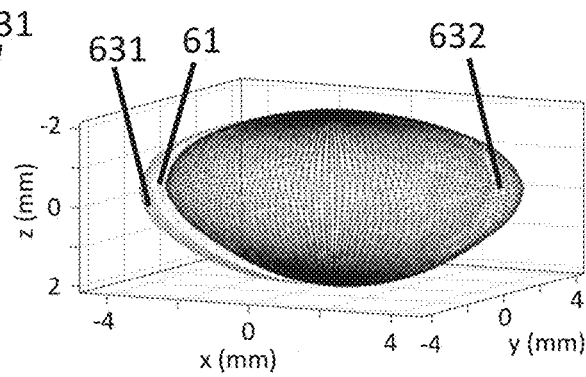
FIG. 6D1
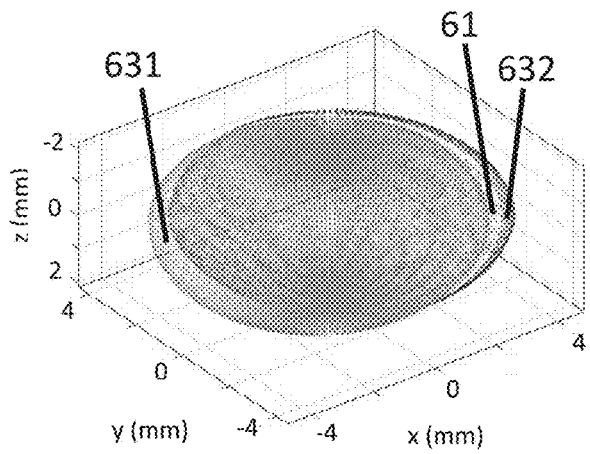
FIG. 6D2
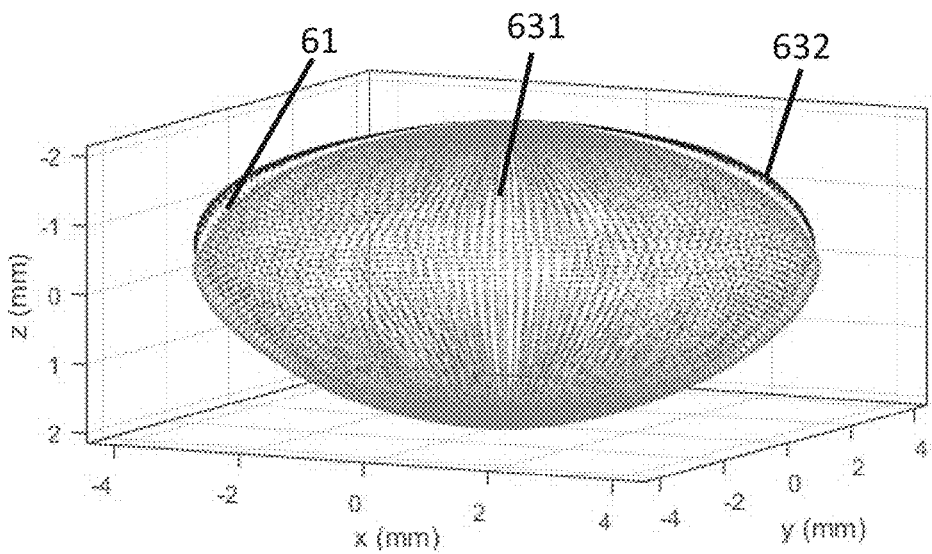
FIG. 6E1

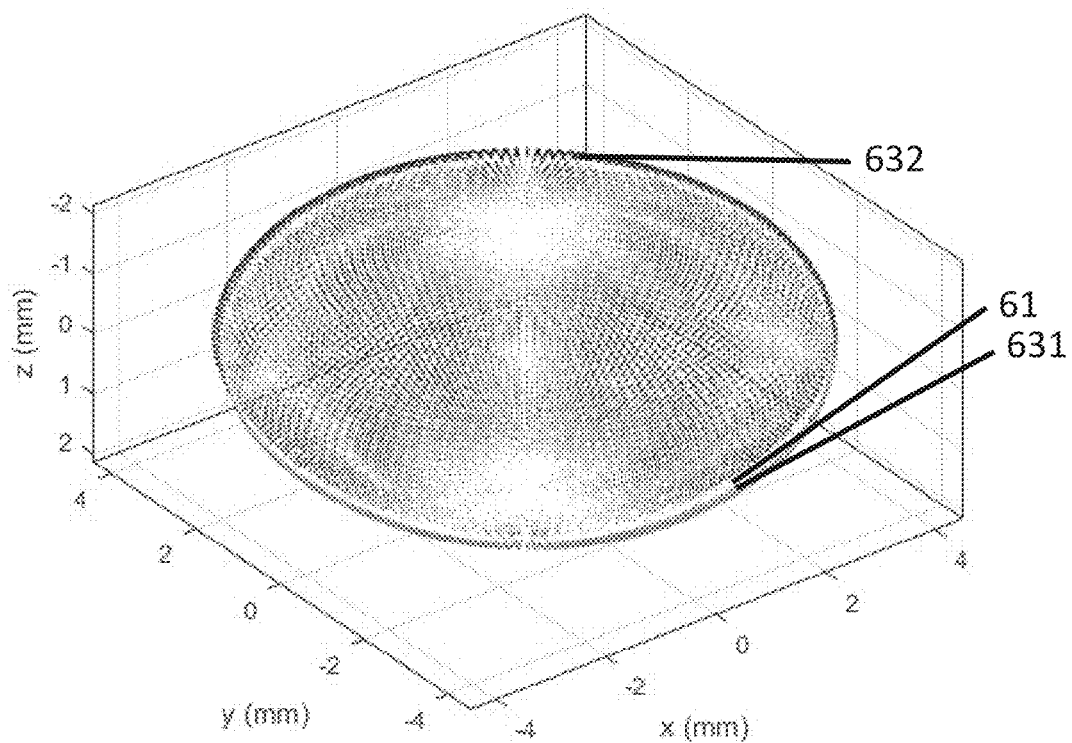
FIG. 6E2
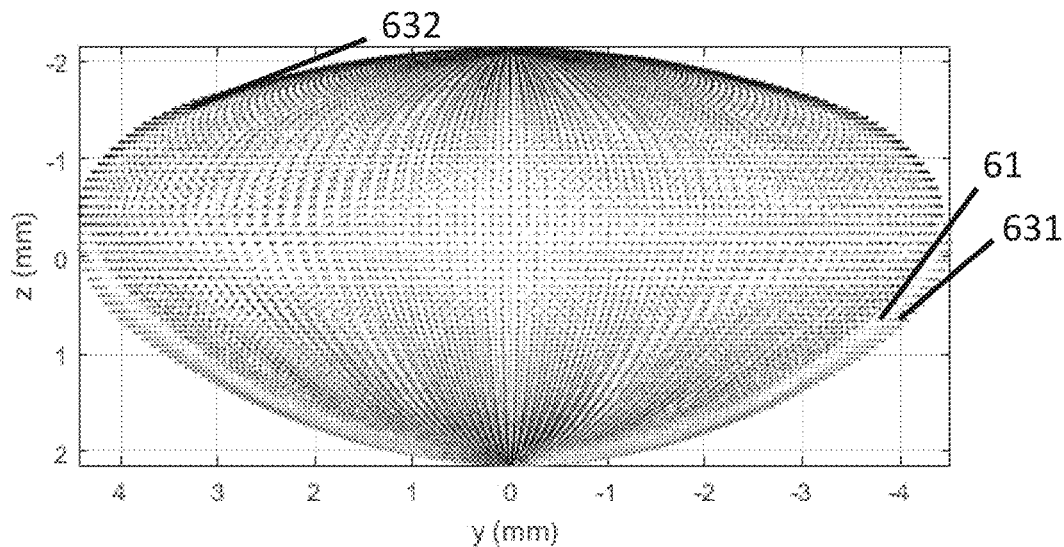
FIG. 6E3

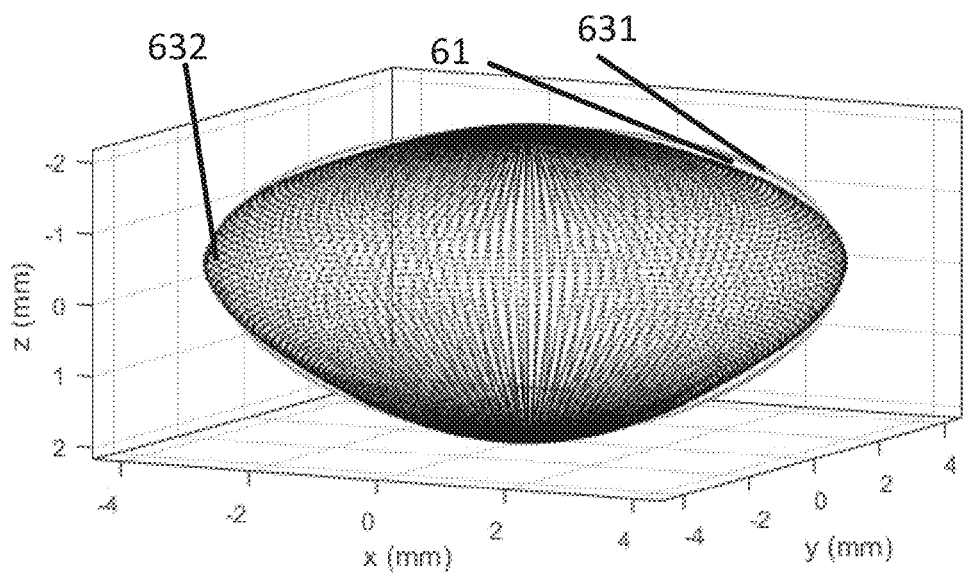
FIG. 6F1
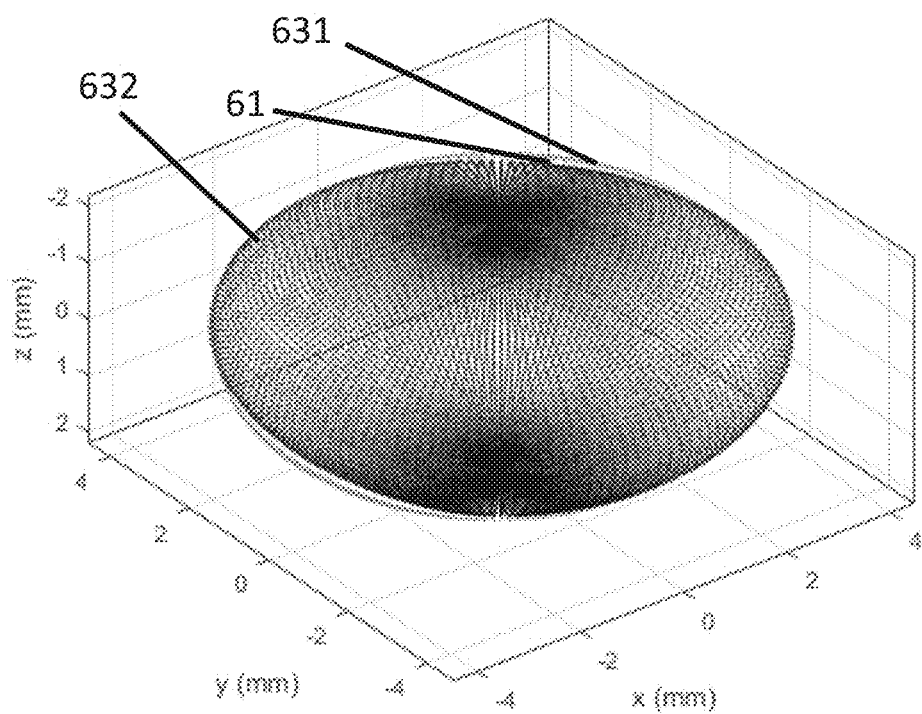
FIG. 6F2

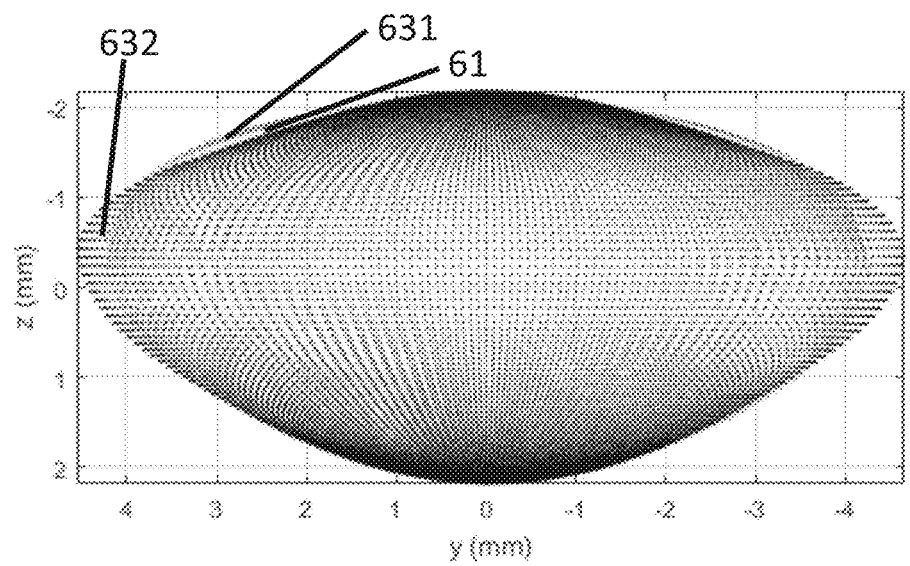
FIG. 6F3
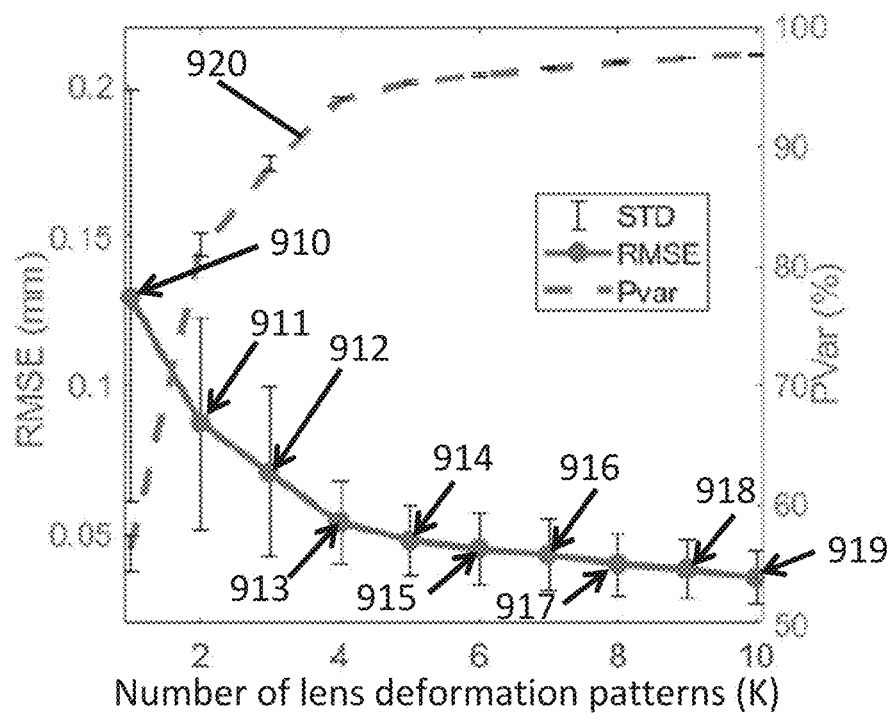
FIG. 7

METHOD OF ESTIMATING A FULL SHAPE OF THE CRYSTALLINE LENS FROM MEASUREMENTS TAKEN BY OPTIC IMAGING TECHNIQUES AND METHOD OF ESTIMATING AN INTRAOCULAR LENS POSITION IN A CATARACT SURGERY

CROSS REFERENCE TO RELATED APPLICATIONS

This application is a continuation-in-part of U.S. patent application Ser. No. 15/583,441 filed May 1, 2017, and claims the benefit of U.S. provisional application No. 62/329,392 filed on Apr. 29, 2016.

BACKGROUND OF THE INVENTION

1. Field of the Invention

The present invention is encompassed within the ophthalmic field and more specifically, it relates to providing precise geometric measurements of a crystalline lens and accurate estimations of an intraocular lens position in a cataract surgery.

2. Description of Related Art

The main optical elements of the eye are the crystalline lens and the cornea. The crystalline lens is the responsible for the focusing ability of the eye (accommodation). Therefore, it is important to understand the properties of the crystalline lens for the design and evaluation of solutions for presbyopia and for cataracts.

There are many studies relating to the geometry of the human crystalline lens, both ex-vivo and in-vivo.

In-vivo measurements of the crystalline lens are typically obtained using Purkinje imaging or Scheimpflug imaging, Magnetic Resonance Imaging (MRI) and Optical Coherence Tomography (OCT). These measurements include lens radii of curvature, lens tilt and decentration, lens internal structure and surface topography and their changes with age and accommodation.

However optical imaging methods only allow to retrieve information visible through the pupil, thereby preventing direct estimation of some important parameters such as the equatorial plane position, EPP, the volume, VOL, the surface area, SA, or the diameter of the lens at the equatorial plane, DIA.

A scarce number of studies have reported in-vivo the shape of the entire lens and associated interesting parameters such as EPP, VOL, SA or DIA. Most of these reports are based on MRI of the lens, which is able to capture non-distorted images of the entire lens. However, MRI-based techniques have significantly lower resolution (around 20-30 times less) and require much higher acquisition times than optical imaging techniques, what makes them not viable for obtaining parameters with the required precision.

Previous approaches to estimate lens geometrical parameters such as VOL, EPP, SA and DIA from optical imaging techniques estimate such parameters by intersecting two parametric surfaces that best fit the available data within the pupil size (PS) of the anterior (AL) and the posterior (PL) surfaces of the lens. However, these methods (in the following referred to as 'intersection approaches') produce an overestimation of the parameters VOL, SA and DIA, and an underestimation the EPP (anterior shift).

Other approaches consider a constant value for the EPP (relative to the lens thickness), although some reports suggest that EPP is subject-dependent.

Patent document WO A2 2011/026068 discloses a method for creating a geometric model of an ocular lens capsule using the radii of curvature of the anterior and the posterior lens surfaces and the lens thickness previously determined by Scheimpflug imaging. As this method relies on an intersection approach, it is subject to the problems explained above.

Also, patent document US A 2010/121612 discloses a method for characterizing an entire lens surface including anterior and posterior hemispheres as well as the equatorial region as a single continuous mathematical representation. The method disclosed is based on shadow photogrammetry of eye tissues which provides the full lens contour. It is only valid ex-vivo.

Therefore, there is a need for a method which provides an estimation of the full geometry or shape of the crystalline lens, especially in-vivo, and/or of the capsular bag and at the same time reduces the estimation error with respect to known methods.

Preoperative estimation of postoperative IOL position (ELP) is the largest contribution of error to the modern IOL power calculation ("*Sources of error in intraocular lens power calculation*" Norrby S., Journal of Cataract & Refractive Surgery 2008; 34:368-376). Therefore, any improvement in postoperative IOL position prediction will provide better IOL power selection and thus refractive and visual outcomes using typical formulas or ray tracing-assisted IOL power calculation.

Different preoperative variables have been used in the design of formulas for the prediction of post-operative IOL position, so-called estimated lens position (ELP). For example, the widely used SRK/T formula ("*Development of the SRK/T intraocular lens implant power calculation formula*", Retzlaff J. A., Sanders D, Kraff M, Journal of Cataract & Refractive Surgery 1990; 16:333-340) uses the axial length and anterior corneal quantification to predict the IOL position; the Haigis formula ("*The Haigis formula*", Haigis W, In: Shammas HJ (ed). Intraocular lens power calculations. Thorofare, N.J.: Slack Inc. 2004; 5-57) uses the axial length and preoperative ACD; or the Olsen formula ("*Prediction of the effective postoperative (intraocular lens) anterior chamber depth*", Olsen T, Journal of Cataract & Refractive Surgery 2006; 32:419-424), which employs a 5-variable model, in which the input parameters are the axial length, the preoperative ACD, the lens thickness, the average corneal radius and the preoperative refraction. A comprehensive review can be found in ("*Calculation of intraocular lens power: a review*", Olsen T, Acta Ophtalmologica 2007; 85:472-485, Table 5). In most approaches, ELP is estimated from parameters unrelated with the shape of the crystalline lens. Reported approaches using some information on the crystalline lens use axial measurements (1-dimensional) or 2-dimensional models/measurements that never includes the full shape of the crystalline lens, with intuitively seems critical to accurately estimate the postoperative IOL position (as the IOL will be placed inside the capsular bag of the crystalline lens).

U.S. patent application Ser. No. 15/583,441 filed by the same applicant, discloses a method of estimating a full shape of a crystalline lens of an eye from measurements of the lens taken in-vivo by optical imaging techniques, the measurements comprising visible portions of the crystalline lens, the method comprises defining non-visible portions of the lens parting from the in-vivo measurements and using a geometrical model of a lens previously built from ex-vivo measurements; U.S. Ser. No. 15/583,441 also discloses a method for estimating an IOL position from parameters obtained from the quantification of the full shape of the crystalline lens, such as VOL, DIA, EPP or SA.

Some embodiments of the method disclosed in U.S. Ser. No. 15/583,441 rely on estimating the full shape of a crystalline lens by fitting the in-vivo measurements to a first parametric surface corresponding to an anterior surface of a crystalline lens and to a second parametric surface corresponding to a posterior surface of a crystalline lens. The first and second parametric surfaces are extrapolated to an extent given by a first parameter to define a central region of the lens. Then, data of a part of the central region of the lens is used to define an equatorial region of the lens by a third parametric surface. Therefore, a plurality of parametric surfaces, wherein each parametric surface represents a different portion of the lens, is used to estimate the full shape of a crystalline lens. Some parameters obtained from the quantification of the full shape such as the VOL, DIA, SA or EPP, are used to estimate the IOL position. However, there is still a need for further improvement in estimation of the full shape of a crystalline lens as well as in estimation of IOL position from the actual full shape of that crystalline lens.

SUMMARY OF THE INVENTION

In the present invention, a method of estimating a full shape of a crystalline lens of an eye is provided, which shape is estimated using measurements taken by optical imaging techniques, such as Optical Coherence Tomography (OCT).

Some examples of applications of the method are: aiding in the design of custom-made intraocular lenses, predicting an estimated lens position of a lens to be implanted in an eye, aiding in the sizing of an accommodative IOL to be implanted in an eye, potentially aiding in prospective surgical techniques for counteracting the effects of presbyopia, such as surgical techniques based on lens refilling (such as the Phaco-Ersatz approach). Another application of the method is to aid in understanding the changes undergone by a crystalline lens during infancy and childhood. Understanding these changes potentially will give insights on the relation between these changes and emmetropization as well as in the potential implication of these changes in the development of refractive errors. At the same time, the method presents the advantage of being applicable in optical imaging, which i is non-invasive.

An aspect of the present invention relates to a method of estimating a full shape of a crystalline lens of an eye, that is, estimating the shape of the whole lamina defining the contour of the lens of an eye. Therefore, the full shape of a crystalline lens of an eye is the shape defined by all the constituent portions of said lamina. The full shape is estimated from measurements of the lens taken in-vivo by optical imaging techniques, the measurements comprising visible portions of the lens. The measurements of the lens taken by optical imaging techniques are taken in-vivo and, therefore, the measurements relate just to those parts of the central anterior portion and the central posterior portion of the lens which result visible through the pupil of the eye. These in-vivo measurements are advantageous to optimize performance of state-of-the-art cataract surgery, because they allow to construct patient-specific eye models in order to predict the best IOL to be implanted in a given patient. The optical imaging techniques used in the disclosed method can be one or more of Purkinje or Scheimpflug imaging techniques or Optical Coherence Tomography, OCT.

The method comprises the following steps:
receiving, by a data-processing system, the in-vivo measurements of the lens,
determining, by the data-processing system, non-visible portions of the lens parting from the in-vivo measurements. The non-visible portions are those portions of the lens which are not visible through the pupil of the eye because the iris obstructs the light. That is, the non-visible portions of the lens comprise those portions of the lens which join the measured central anterior portion with the measured central posterior portion of the lens. This junction takes place by direct contact between the non-visible portions and the measured central anterior portion of the lens and by direct contact between the non-visible portions and the measured central posterior portion of the lens. Therefore, the non-visible portions of the lens comprise the equator of the lens.

The step of determining the non-visible portions of the lens comprises:

a) establishing a location of a first plurality of points which defines an initial full shape of a crystalline lens of an eye, b) displacing the first plurality of points a plurality of lengths following a plurality of directions to a location of a second plurality of points. The second plurality of points are estimated points of the full shape of the lens of which the in-vivo measurements have been taken. The initial full shape of a crystalline lens is obtained from ex-vivo measurements, and the plurality of lengths is estimated from the in-vivo measurements. In this way, in order to estimate the full shape of a particular lens of an eye it is not required to adapt the first plurality of points to the in-vivo measurements, only the plurality of displacement lengths need to be adapted to the in-vivo measurements. In some of these embodiments, the plurality of directions followed by the plurality of lengths is built from ex-vivo measurements and hence does not need to be adapted to the in-vivo measurements. This is advantageous because processing resources are not consumed for adapting the plurality of directions to particular in-vivo measurements.

This way, the full shape of a crystalline lens of an eye is estimated by displacing the first plurality of points which defines an initial full shape of a crystalline lens of an eye. Therefore, in the present method it is not required to assign different geometric functions to different regions of the estimated full shape, and the present method allows describing the full shape of any crystalline lens with a very small number of variables.

Since the first plurality of points is built from ex-vivo measurements, the initial full shape of a crystalline lens is suitable for being built prior to taking the in-vivo the measurements.

In some embodiments, the step of displacing the first plurality of points a plurality of lengths following a plurality of directions to a location of a second plurality of points comprises displacing according to at least one lens deformation pattern, wherein the at least one lens deformation pattern is obtained from ex-vivo measurements. Thereby, the full shape of a crystalline lens is estimated by means of deforming an initial full shape of a crystalline lens. Each lens deformation pattern is a deformation pattern of the full shape of a crystalline lens. In other words, each lens deformation pattern is not limited to a deformation of a particular reduced portion of the full shape of the lens and different lens deformation patterns may specify details of the same portion of the full shape. Therefore, the lens deformation patterns may be seen as functions, each function representing a full shape of a crystalline lens. In addition, since the at least one lens deformation pattern is built from ex-vivo measurements, the at least one lens deformation pattern is suitable for being built prior to taking the in-vivo the measurements.

In some embodiments, each lens deformation pattern defines a ratio for each pair of points which are displaced according to the lens deformation pattern, each ratio being a ratio between a length of displacement of a point of the pair of points and a length of displacement of the other point of the pair of points. In this way, each lens deformation pattern defines a particular relative displacement between every point of the full shape of a lens, wherein these relative displacements can be proportionally scaled. Each lens deformation pattern itself can be represented with a full shape of a lens.

In some embodiments, the plurality of lengths of step b) are obtained by applying a weight coefficient to each of the at least one lens deformation pattern. The weight coefficient(s) is/are estimated from the in-vivo measurements. Thereby the length of displacement of each point of the initial full shape of a crystalline lens is obtained by applying a weight coefficient, obtained from in-vivo measurements, to each of the at least one lens deformation pattern, obtained from ex-vivo measurements. In other embodiments more than one coefficient may be applied to each lens deformation pattern, however an advantage of applying just one coefficient to each deformation pattern is that the estimation method is simpler and requires fewer processing resources.

In some embodiments, the step of displacing the first plurality of points is performed according to the following equation, which comprises a linear combination of the at least one lens deformation pattern:

$$l = l_0 + \sum_{k}^{K} a_k e_k$$

where:

l is a matrix which contains coordinates of the second plurality of points resulting from displacing the first plurality of points, $l_0$ is a matrix which contains coordinates of the first plurality of points, $e_k$ is a matrix which defines a k lens deformation pattern of the at least one lens deformation pattern, the $e_k$ matrix defining displacements of the first plurality of points, $a_k$ is a k scalar weight coefficient of the at least one weight coefficient, K is a total number of lens deformation patterns used to estimate the full shape of the lens.

In other embodiments, the step of displacing the first plurality of points is performed according to an equation which comprises a non-linear combination of the at least one lens deformation pattern. However, an equation comprising a linear combination of the at least one lens deformation pattern, instead of a non-linear combination, is preferable due to its higher simplicity and because allows obtaining accurate estimations of a full shape of a crystalline lens.

In certain embodiments, each lens deformation pattern is an eigenvector of a covariance matrix of residual data, wherein the residual data are a difference between a full shape of each lens of a set of ex-vivo lenses and an average full shape of the set of ex-vivo lenses. In this way, since each lens deformation pattern is an eigenvector, it can be determined which lens deformation patterns explain more variance of the full shape of a crystalline lens.

In some embodiments, each weight coefficient applied to each lens deformation pattern is estimated from at least one secondary coefficient wherein each of the at least one secondary coefficient is a coefficient applied to a deformation pattern of a central anterior portion and of a central posterior portion of a full shape of a crystalline lens of an eye. The at least one secondary coefficient is such that when applied to the at least one deformation pattern of a central anterior portion and of a central posterior portion gives as a result a deformation of the central anterior portion and of the central posterior portion which allows estimating the shape of the central anterior portion and of the central posterior portion of the in-vivo measured lens. In these embodiments, the method comprises the step of calculating the at least one secondary coefficient applied to a deformation pattern of a central anterior portion and of a central posterior portion of a full shape of a crystalline lens. The at least one deformation pattern of a central anterior portion and of a central posterior portion is obtained from ex-vivo measurements, and the at least one secondary coefficient is calculated from the in-vivo measurements. This way of estimating the full shape of a crystalline lens can be seen as an estimation of a full shape of a crystalline lens from an estimation of the central anterior portion and of the central posterior portion of the lens, which may be visible through the pupil.

In the present disclosure, the expression "weight coefficient" refers to a weight coefficient of a lens deformation pattern unless it is explicitly said that the weight coefficient is a weight coefficient of a deformation pattern of an anterior and of a posterior portion of a full shape of a lens. For the sake of conciseness, a weight coefficient of a deformation pattern of an anterior portion and of a posterior portion of a full shape of a lens has been referred to as "secondary coefficient" in the present disclosure.

In some embodiments, the method further comprises estimating the at least one weight coefficient of a lens deformation pattern as a function of estimated geometric parameters of the lens measured in-vivo. The estimated geometric parameters being estimated from the in-vivo measurements. In addition, the geometric parameters are characteristic geometric parameters of a shape of a crystalline lens such as lens thickness, radius of curvature of an anterior surface of the lens, radius of curvature of a posterior surface of the lens or Zernike coefficients describing surfaces of the lens. Thereby an estimate of a full shape of a crystalline lens can be obtained from characteristic geometric parameters of a shape of a crystalline lens.

In some embodiments, the at least one weight coefficient consists of more than three weight coefficients. This way, a higher accuracy can be achieved in the estimation of a full shape of a lens using just a few weight coefficients.

In some embodiments, a lens volume and/or a lens surface area and/or a lens diameter and/or a lens equatorial position of the in-vivo measured lens are/is estimated as a function of the at least one weight coefficient. The method of the present invention may be advantageously used to obtain a preoperative estimation of the volume VOL of the crystalline lens, which is of high value in emerging treatments of presbyopia. In particular, knowledge of a lens volume is important in lens refilling techniques, in which the degree of filling of the capsular bag is essential to achieve the appropriate refraction and an adequate amplitude of accommodation. The lens volume VOL is also very important in the selection of several accommodative IOLs (A-IOLs), where prior knowledge of the DIA and VOL may enhance refractive predictability and be critical for the correct mechanism of action of the A-IOL.

Another aspect of this invention relates to a method of predicting an estimated lens position of an intraocular lens implantable in an eye, wherein the estimated lens position is obtained from the full shape of the in-vivo measured lens, the full shape of the in-vivo measured lens being estimated using a method defined in the foregoing. This is advantageous because the estimated lens position may be predicted preoperatively, that is the estimated lens position may be predicted from a full shape of a crystalline lens which has been estimated preoperatively.

In some embodiments, the estimated lens position of a lens implantable in an eye is obtained using the following formula:

$$ELP = C_0 + \sum_k^K a_k C_k$$

wherein ELP is the estimated lens position;

$a_k$ is a k scalar weight coefficient of the at least one weight coefficient;

$C_k$ is a k positioning weight coefficient that multiplies the weight coefficient $a_k$;

$C_0$ is a bias term.

In this way, it is possible to obtain, from the at least one weight coefficient, an estimated lens position of a lens yet to be implanted in the eye.

Still a further aspect of the present invention relates to a method of selecting an intraocular lens implantable in an eye, which comprises using the method a method of predicting an estimated lens position of an intraocular lens implantable in an eye previously defined to calculate the estimated lens position of the intraocular lens. Having an accurate estimation of the full shape of the crystalline lens results in a better selection of the IOL power of the lens to be implanted in a cataract surgery. The IOL power may be calculated based on ray tracing or on IOL power formulas.

Another aspect of the present invention relates to a method of estimating a full shape of a crystalline lens of an eye from measurements of the lens taken by optical imaging techniques. This method comprises:

a) estimating at least one weight coefficient from the measurements;

b) applying (for example, multiplying) a lens deformation pattern to each at least one weight coefficient to obtain a plurality of lengths of displacement, wherein the at least one lens deformation pattern is obtained from ex-vivo measurements;

c) displacing a first plurality of points the plurality of lengths of displacement obtained in step b) to a location of a second plurality of estimated points of the full shape of a lens.

The present invention also relates to a data-processing system configured to determine a full shape of a crystalline lens of an eye by means of displacing a first plurality of points a plurality of lengths following a plurality of directions to a location of a second plurality of points, wherein the first plurality of points defines an initial full shape of a crystalline lens of an eye, the initial full shape is obtained from ex-vivo measurements, and the plurality of lengths is obtained by applying a weight coefficient to each of at least one lens deformation pattern.

In this way, the data-processing system can be used to generated full shapes of crystalline lenses.

The data-processing system can be used to simulate several lenses with different shapes in order to assess their performance when subjected to determined conditions. These simulations may be used to improve the biomechanical models of the crystalline lens. This improvement directly benefits the computational modelling of the accommodative process and to the design of customized intraocular lenses. In addition, this simulation may be used to select a more appropriate intraocular lens to be implanted in an eye. Furthermore, this simulation may be used to determine more accurately an amount of fluid required for a particular lens-refilling surgery.

In some embodiments, the data-processing system is configured to determine the full shape of a crystalline lens by means of changing the at least one weight coefficient while keeping the at least one lens deformation pattern constant and while keeping the initial full shape of a crystalline lens constant. This is advantageous because just a few parameters (the weight coefficients) need to be changed in order to generate a meaningful full shape change.

The present invention also relates to a data-processing system which comprises processing means for carrying out one or more of the methods defined and disclosed in the foregoing.

In some embodiments, the data-processing system comprises processing means for generating a realistic full shape of a crystalline lens, wherein the realistic full shape of a crystalline lens is defined by assigning values to the at least one weight coefficient, wherein the value of each of the at least one weight coefficient is within an interval defined by a minimum and a maximum value obtained from the ex-vivo measurements. Constraining the values of the at least one weight coefficient to certain intervals obtained from the ex-vivo measurements is advantageous because allows ensuring that the generated lenses are more realistic. In some of these embodiments, the value of each of the at least one coefficient is within an interval defined by the maximum value and the minimum value of said weight coefficient for a set of ex-vivo lenses from which the ex-vivo measurements have been obtained. These maximum and minimum values are advantageous, when compared to other maximum and minimum values, because they are easily determined. Other maximum and/or minimum values are in general obtainable, for example, by means of testing whether these higher maximum and lower minimum values result in a realistic full shape of a crystalline lens.

In some embodiments the data-processing system is used to generate random full shapes of a lens of an eye in the aforementioned simulations. The random full shape of the crystalline lens can be defined by assigning values to the at least one weight coefficient, wherein said values are randomly taken from a probability distribution selected from a number of predetermined probability distributions. The random values can be additionally constrained in order to generate full shapes of lenses which are more realistic.

In some embodiments, the values assigned to the at least one weight coefficient are randomly taken from a probability distribution selected from a number of predetermined probability distributions, wherein each probability distribution of the number of predetermined probability distributions is for a particular age range. The full shape of a crystalline lens of an eye changes as the lens ages and the particular effect that aging has on the shape of a lens and hence on the performance of the lens can be assessed by means of assessing a plurality of lenses for a particular age. Thereby the probability of a patient having a crystalline lens with a particular defect may be determined and hence make it easier for an ophthalmologist to determine the defect of the lens and hence the most suitable remedy to treat the defect.

Another aspect of the invention relates to an optical imaging device comprising a data-processing system as previously defined and disclosed.

It is apparent to the skilled person that the resulting second plurality of points (i.e. the estimated full shape of a crystalline lens) may be shown in an image which may be used for a number of purposes such as being displayed on a screen, processing the image in order to obtain relevant measurements of the full shape of the first lens, monitoring lens volume to assess progress of a certain ocular condition (i.e. diabetes, myopia) choosing an appropriate crystalline or IOL lens from a database and/or manufacturing an IOL lens.

The different aspects and embodiments of the present invention defined in the foregoing may be combined with one another, as long as they are compatible with each other.

Additional advantages and features of the invention will become apparent from the detail description that follows and will be particularly pointed out in the appended claims.

BRIEF DESCRIPTION OF THE DRAWINGS

To complete the description and in order to provide for a better understanding of the invention, a set of drawings is provided. The drawings form an integral part of the description and illustrate embodiments of the invention, which should not be interpreted as restricting, but just as an example of how the invention can be carried out. The drawings comprise the following figures:

FIG. 5A1 shows a first embodiment of a first lens deformation pattern.

FIG. 5A2 shows a second embodiment of the first lens deformation pattern.

FIG. 5B1 shows a first embodiment of a second lens deformation pattern.

FIG. 5B2 shows a second embodiment of the second lens deformation pattern.

FIG. 5C1 shows a first embodiment of a third lens deformation pattern.

FIG. 5C2 shows a second embodiment of the third lens deformation pattern.

FIG. 5D1 shows a first embodiment of a fourth lens deformation pattern.

FIG. 5D2 shows a second embodiment of the fourth lens deformation pattern.

FIG. 5E1 shows a first embodiment of a fifth lens deformation pattern.

FIG. 5E2 shows a second embodiment of the fifth lens deformation pattern.

FIGS. 6A1 to 6A8 illustrate how the first lens deformation pattern deforms a full shape of a crystalline lens, more specifically, FIG. 6A1 shows a first perspective view of three full shapes of crystalline lenses, FIG. 6A2 shows a second perspective view of the three full shapes of lenses; FIG. 6A3 shows a frontal view of the three full shapes of lenses, FIG. 6A4 shows a top view of the three full shapes of lenses, FIG. 6A5 shows a bottom view of the three full shapes of lenses; FIG. 6A6 shows a rear view of the three full shapes of lenses, FIG. 6A7 shows a right side view of the three full shapes of lenses, FIG. 6A8 shows a left side view of the three full shapes of lenses.

FIGS. 6B1 to 6B8 illustrate how the second lens deformation pattern deforms a full shape of a crystalline lens, more specifically, FIG. 6B1 shows a first perspective view of three full shapes of crystalline lenses, FIG. 6B2 shows a second perspective view of the three full shapes of lenses; FIG. 6B3 shows a frontal view of the three full shapes of lenses, FIG. 6B4 shows a top view of the three full shapes of lenses, FIG. 6B5 shows a bottom view of the three full shapes of lenses; FIG. 6B6 shows a rear view of the three full shapes of lenses, FIG. 6B7 shows a right side view of the three full shapes of lenses, FIG. 6B8 shows a left side view of the three full shapes of lenses.

FIGS. 6C1 to 6C3 illustrate how the third lens deformation pattern deforms a full shape of a crystalline lens, more specifically, FIG. 6C1 shows a first perspective view of three full shapes of crystalline lenses, FIG. 6C2 shows a second perspective view of the three full shapes of lenses and FIG. 6C3 shows a lateral view of the three full shapes of lenses.

FIGS. 6D1 and 6D2 illustrate how the fourth lens deformation pattern deforms a full shape of a crystalline lens, more specifically, FIG. 6D1 shows a first perspective view of three full shapes of crystalline lenses and FIG. 6D2 shows a second perspective view of the three full shapes of lenses.

FIGS. 6E1 to 6E3 illustrate how the fifth lens deformation pattern deforms a full shape of a crystalline lens, more specifically, FIG. 6E1 shows a first perspective view of three full shapes of crystalline lenses, FIG. 6E2 shows a second perspective view of the three full shapes of lenses and FIG. 6E3 shows a lateral view of the three full shapes of lenses.

FIGS. 6F1 to 6F3 illustrate how the sixth lens deformation pattern deforms a full shape of a crystalline lens, more specifically, FIG. 6F1 shows a first perspective view of three full shapes of crystalline lenses, FIG. 6F2 shows a second perspective view of the three full shapes of lenses and FIG. 6F3 shows a lateral view of the three full shapes of lenses.

FIG. 7 is a graph which shows values of the arithmetic mean and the standard deviation across lenses of the root mean squared error (RMSE) and values of the arithmetic mean and the standard deviation of PVar in the estimation of a full shape of a crystalline lens, each value corresponding to a selection of a particular number of lens deformation patterns.

FIG. 8 is a graph which shows values of the arithmetic mean and the standard deviation of the root mean squared error (RMSE) in the estimation of a full shape of a crystalline lens, each value corresponding to a particular method of estimating a full shape of a crystalline lens; some of these methods form part of the State-of-the-art.

DETAILED DESCRIPTION OF THE PREFERRED EMBODIMENTS

Figures 1A, 1B:
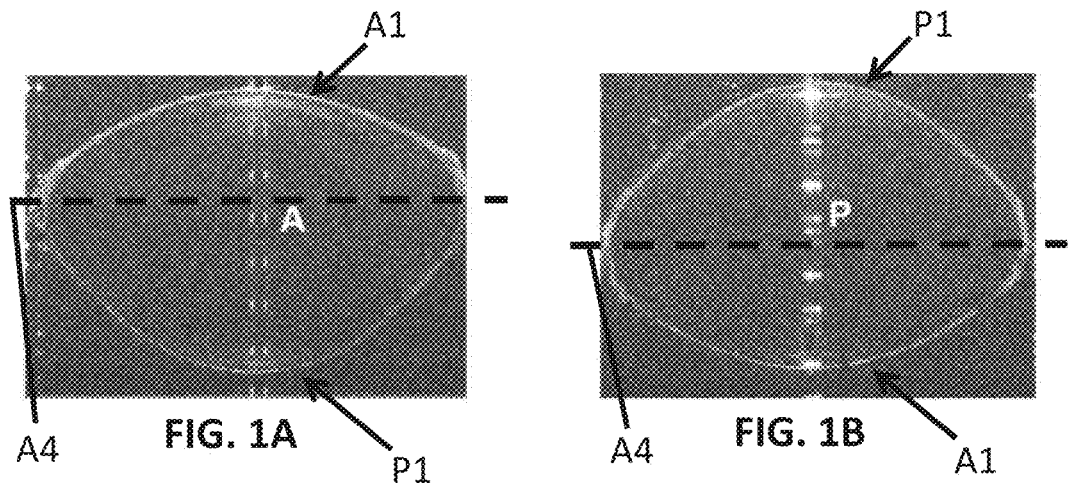
FIG. 1A shows a first example of a B-scan of a crystalline lens.
FIG. 1B shows a second example of a B-scan of a crystalline lens.

The following description is not to be taken in a limiting sense but is given solely for the purpose of describing the broad principles of the present invention. Embodiments thereof will be described by way of example, with reference to the above-mentioned drawings.

Below it is described an example of a method of estimating a full shape of a crystalline lens of an eye according to the present invention. The example is part of the following study which complied with the tenets of the Declaration of Helsinki and was approved by the Institutional Review Boards of CSIC, BST, and LVPEI.

3-D digital models of the full shape of each of 133 isolated crystalline lenses were built. The 133 isolated crystalline lenses came from 112 human donors. 28 crystalline lenses coming from 24 donors were isolated from eye globes obtained from the eye bank "Banc de Sang i Teixits", a.k.a "BST" (Bacelona, Spain). The age range of the donors from the BST eye bank was 19-71 years old (i.e. y/o), had an arithmetic mean of 48 y/o and a standard deviation of 13 y/o. The remaining 105 crystalline lenses, which came from 88 donors, were isolated from eye globes obtained from the eye bank "Ramayamma International Eye Bank at LVPrasad Eye Institute", a.k.a. "LVPEI" (Hyderabad, India). The age range of the donors from the LVPEI eye bank was 0-56 y/o, had an arithmetic mean of 26 y/o, and a standard deviation of 14 y/o.

The following procedure was followed to separate the crystalline lenses from the eye globes. After enucleation of an eye globe, a surgeon carefully isolated the crystalline lens from the eye globe and immediately placed it on a custom-made lens holder of nylon sutures within a cuvette filled with a preservation media. The preservation media used for the crystalline lenses of the "BST" eye bank was "DMEM/F-12 HEPES no phenol red, GIBCO". The preservation media used for the crystalline lenses of the "LVPEI" eye bank was "BSS, Alcon Laboratories". The lens holder was advantageous because prevented contact between the crystalline lens and the bottom of the cuvette.

Initially 157 crystalline lenses were measured. However, those crystalline lenses which comprised detachments of a lens capsule and those crystalline lenses which showed any kind of apparent damage were excluded from further study, remaining 133 lenses.

The lenses from the "BST" eye bank were measured with a custom developed spectral domain optical coherence tomography (SD-OCT) system which used a superluminescent diode as a light source with a central wavelength of 840 nm and a full width at half maximum (FWHM) bandwidth of 50 nm. The axial range was of 7 mm in air, resulting in pixels having a size of 3.4 µm in the axial dimension with an optical resolution in the axial dimension of 6.9 µm in tissue. The acquisition speed was of 25000 A-scans/s and each 3-D digital model of a full shape of a crystalline lens was composed of 60 B-scans on a 12×12 mm lateral area of the crystalline lens and 1668 A-scans per B-scan.

The lenses from the "LVPEI" eye bank were measured with a different SD-OCT system which is the commercial imaging system ENVISU R4400, Bioptigen Inc. equipped with a superluminescent diode as a light source with a central wavelength of 880 nm and a FWHM bandwidth of 40 nm. The axial range was of 15.18 mm in air, resulting in pixels having a size of 7.4 µm in an axial dimension with an optical resolution of 6.4 µm in tissue in the axial dimension. The acquisition speed was of 32000 A-scans/s and each 3-D digital model of a full shape of a crystalline lens was composed of 100 B-scans on a 15×15 mm lateral area and 600 A-scans per B-scan.

The crystalline lenses were aligned with the corresponding OCT system to collect B-scans of the full shape of the crystalline lenses, such that each B-scan contained a cross-section of the crystalline lens, the cross-section being parallel to a plane containing the apex of the anterior portion and the apex of the posterior portion of the crystalline lens. The crystalline lenses were first scanned with their anterior portion facing the light beam of the OCT system. Several B-scans were performed in this position of the crystalline lens with respect to the OCT system. FIG. 1A shows an example of a B-scan A of a crystalline lens which anterior portion A1 is facing the light beam of an OCT system while the crystalline lens is being scanned with the OCT system. The light source of the OCT system emits a light beam which approaches the lens from the upper part of the FIG. 1A and enters the lens through the anterior portion A1 of the lens.

Thereafter, each crystalline lens was flipped over and scanned with its posterior portion facing the OCT beam. Several B-scans were performed in this position of the crystalline lens with respect to the OCT system. FIG. 1B shows an example of a B-scan P of a crystalline lens which posterior portion P1 is facing the light source of the OCT system while being scanned by the OCT system. The light source of the OCT system emits a light beam which approaches the lens from the upper part of the FIG. 1B and enters the lens through a posterior portion P1 of the lens.

In addition, each of FIGS. 1A and 1B shows an equatorial plane A4 of a crystalline lens.

Figure 2:
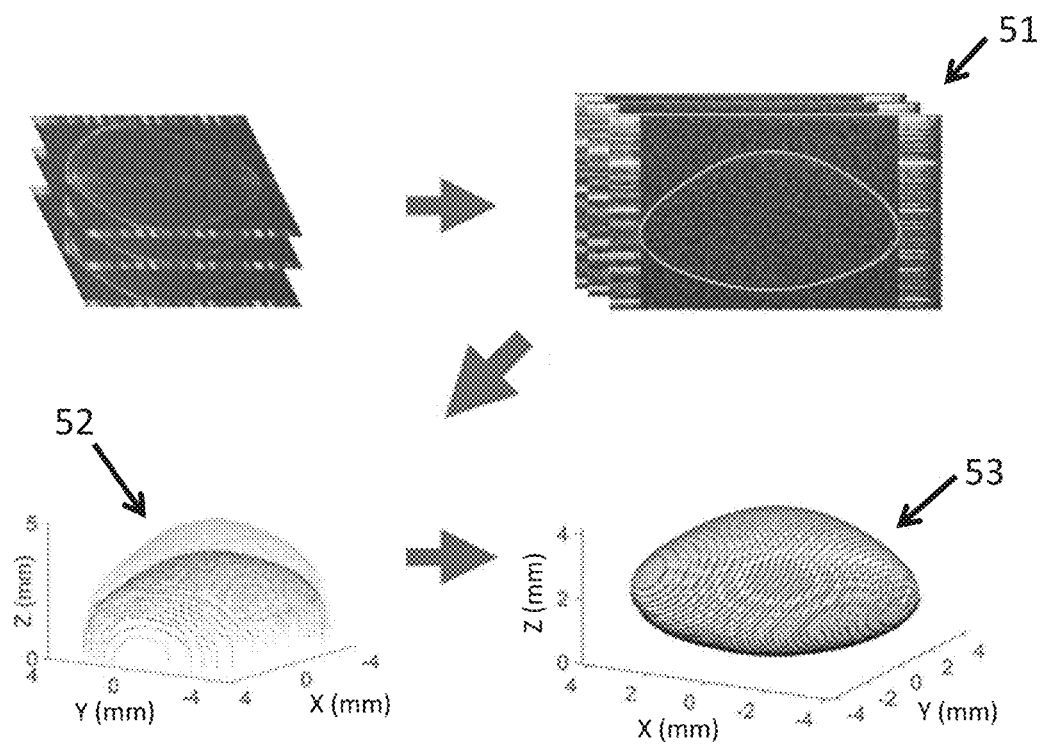
FIG. 2 schematically illustrates an exemplary method for obtaining a 3-D digital model of a full shape of a crystalline lens from B-scans of the crystalline lens.

FIG. 2 schematically illustrates the main steps for obtaining a 3-D digital model of a full shape of a crystalline lens from the B-scans. The main steps for obtaining the 3-D digital model were: segmentation of the B-scans (51), distortion correction (52) and tilt removal and registration (53). In the segmentation of the B-scans, the full shape of a lens was automatically segmented in each B-scan using thresholding, Canny edge detectors, morphological operations, and a-priori knowledge of the measurements, resulting in 3-D data composed of the segmentation of all the B-scans. Then the 3-D data composed of the segmentation of all the B-scans were fit with Zernike polynomials of up to the 4-th order, and the resulting smooth surface defined by the Zernike polynomials was used to refine the segmentation iteratively. This process was repeated applying the segmentation to three different orientations of the B-scans.

The fan distortion present in the segmented surfaces from each B-scan was corrected. The fan distortion arose from the scanning architecture and the optics of the SD-OCT system.

Note that the 3-D digital model of the full shape of a lens was composed of the segmentation of the B-scans of a full-shape of a crystalline lens measured with the anterior surface A1 facing the OCT beam and with the posterior surface P1 facing the OCT beam as explained previously and shown in FIGS. 1A and 1B. Specifically, the measurements of the anterior surface A1 of the full lens taken with the anterior surface A1 facing the OCT beam and the measurements of the posterior surface P1 of the full lens taken with the posterior surface P1 facing the OCT beam were merged in the construction of the 3-D digital model of the full shape of a lens. The advantage of doing this is that the alterations of the measurements of the anterior A1 and posterior surfaces P1 due to refraction in previous optical surfaces and due to the gradient refractive index (GRIN) of the crystalline lens are minimized.

The distortion of the 3-D digital model of the full shape of a crystalline lens due to the presence of the preservation media was corrected by dividing the geometrical sag of the surfaces by the group refractive index of the preservation media, the group refracting index being 1.345 for the "DMEM/F-12 HEPES no phenol red, GIBCO" at 840 nm and "BSS, Alcon Laboratories" at 880 nm.

The tilt of the corrected anterior and posterior surfaces of the 3-D digital model of the full shape of a crystalline lens was removed, and both surfaces were combined in order to generate a full shape of a lens. In this combination, the anterior and posterior surfaces were positioned in the same cartesian coordinate system, such that the center of the equator of the anterior and posterior 3-D models matched in the X-Y plane. This merging of the anterior and posterior surfaces is schematically shown in step 53 of FIG. 2. Then, to account for possible rotations when flipping the lens over, one of the surfaces was rotated with respect to the other surface in order to maximize the overlapping between them. Registration in the Z axis was performed by matching the central thickness (LT) of the lens, that was calculated independently using the optical thickness obtained from the OCT scans, the index of refraction of the preservation media and the deformation in the image of the cuvette. In this context the central thickness of the lens is to be understood as the thickness of the lens which goes from the apex of the anterior surface of the lens to the apex of the posterior surface of the lens.

Thereby, a 3-D digital model of the full shape of each of the 133 crystalline lenses was obtained. From these models a location of a first plurality of points defined by an average of the full shape of the 133 crystalline lenses was obtained. In order to simplify the mathematical operations with the 3-D digital models, each model was defined in spherical coordinates through the following steps:

Step 1: The origin 0 of the spherical coordinate system for a 3-D digital model was located laterally, that is located with respect to axes X and Y, in the center of the equator of the 3-D digital model of the full shape of the crystalline lens. The origin 0 of the coordinate system was located axially, that is located with respect to axis Z, at the midpoint of the central thickness LT of the lens previously calculated.

Figure 3:
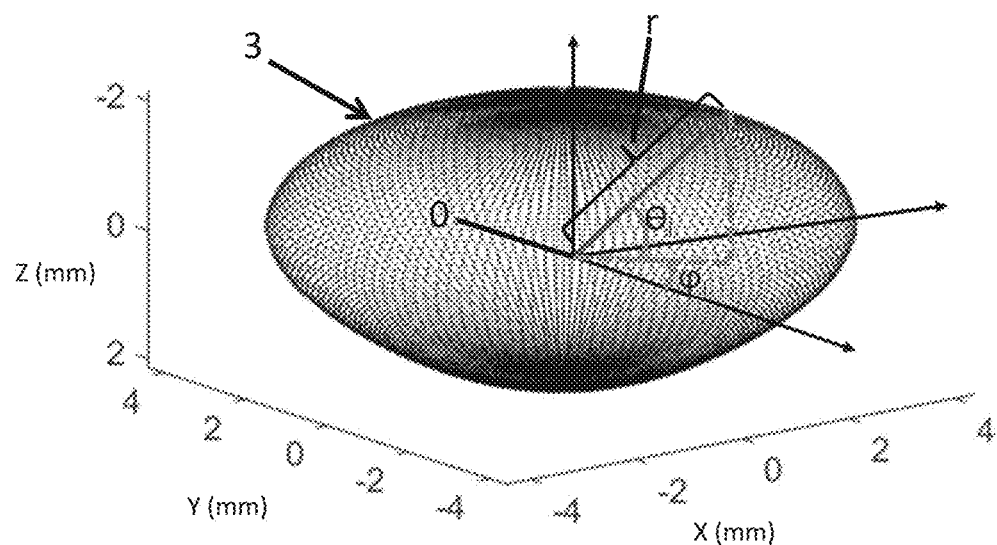
FIG. 3 shows an example of an average full shape of a crystalline lens.

Step 2: The location of each segmented point for a 3-D digital model, the segmented points resulting from the previous segmentation of the B-scans, was defined in spherical coordinates (r, θ, φ) with respect to the origin obtained in previous step 1, wherein r is the distance from the segmented point to the origin of coordinates 0, θ is the elevation angle and φ is the azimuth angle. These coordinates are shown in FIG. 3.

Step 3: The 3-D digital model was sampled at 10000 points, defined by Q=100 azimuth angles $\varphi_j$, each of which was combined with P=100 elevation angles $\theta_i$. The Q=100 azimuth angles $\varphi_j$ were uniformly spaced in the interval $[-\pi, \pi]$, and the P=100 elevation angles $\theta_i$ were uniformly spaced in the interval $$\left[\frac{-\pi}{2}, \frac{\pi}{2}\right].$$

Note that, although this particular sampling procedure does not give rise to evenly placed points on the surface of a sphere, it was observed that lens deformation patterns resulting from different dense samplings were very similar, and this sampling procedure was chosen due to its higher simplicity.

Step 4. For every pair $(\theta_i, \varphi_j)$, i∈[1, . . . , P], j∈[1, . . . , Q], the distances $r_{\theta i, \varphi j}$ from the origin of coordinates 0 to the surface of the full shape of the lens, were obtained. The positions of the aforementioned 10000 sampled points were calculated by cubic interpolation from the segmented points resulting from the previous segmentation of the B-scans. This led to a vector of P×Q elements, each element defining the location of a point of the 3-D model:

$$l_n = [r_{\theta 1, \varphi 1}, r_{\theta 1, \varphi 2}, \ldots, r_{\theta P, \varphi Q}]_n \quad (1)$$

where $l_n$ is the 3-D digital model of a full shape of a crystalline lens "n" of the 133 crystalline lenses.

Step 5. The average lens $\bar{l}$ was obtained as the mean of the vectors $l_n$ of the 133 crystalline lenses:

$$\bar{l} = \frac{1}{133}\sum_{n=1}^{133} l_n \quad (2)$$

In this way, an average of the full shape of the 133 crystalline lenses (hereinafter referred to as "average lens") was obtained from ex-vivo measurements. This average lens established the location of a first plurality of points which defined an initial full shape of a crystalline lens of an eye. An exemplary average 3 of the full shape of the 133 crystalline lenses is shown in FIG. 3.

Thereafter, the lens deformation patterns were obtained from residual data $\Delta_n$ of each 3-D digital model of the 133 crystalline lenses. The residual data $\Delta_n$, as shown in FIG. 4, were obtained as a deviation between the 3-D digital model of each of the 133 crystalline lenses with respect to the average lens:

$$\Delta_n = l_n - \bar{l} \quad (3)$$

Figure 4:
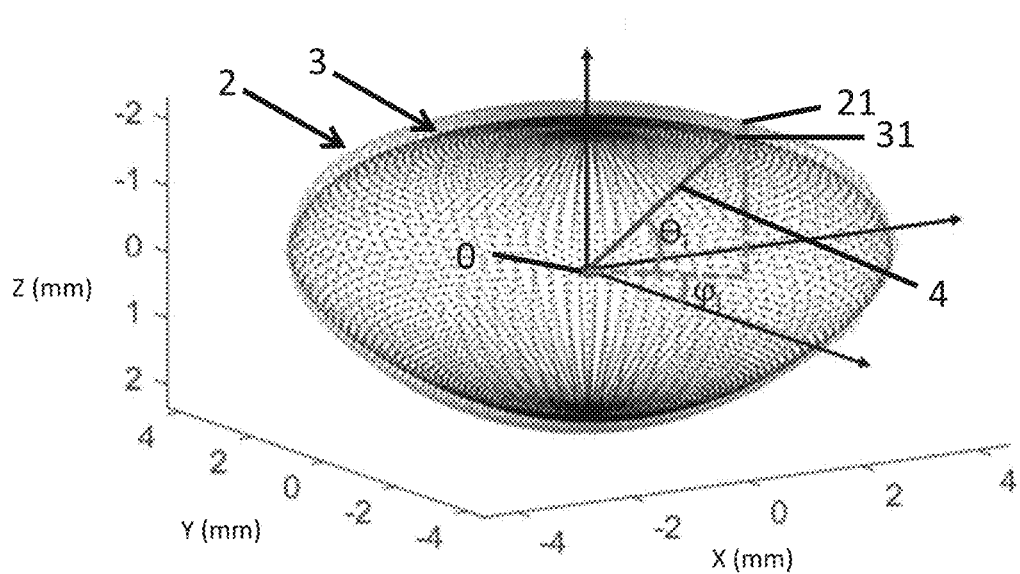
FIG. 4 illustrates a subtraction of an average full shape of a crystalline lens from a particular full shape of a particular crystalline lens.

FIG. 4 shows an example of a way of determination of the residual data $\Delta_n$ which correspond to a point of a 3-D digital model of a full shape 2 of a crystalline lens of the 133 crystalline lenses. These residual data consist of the distance between a point 21 of the 3-D digital model of the full shape 2 of the crystalline and a point 31 of the average lens 3. The point 21 of the 3-D digital model of the full shape 2 of the crystalline lens and the point 31 of the average lens 3 are the intersection points of a straight line 4 having an elevation angle of $\theta_i$, an azimuth angle of $\varphi_i$ and containing the origin of coordinates 0 with the 3-D digital model of the full shape 2 and the average lens 3 respectively.

Step 6. The covariance matrix C of the residual data of the 133 3-D digital models was obtained in order to perform Principal Component Analysis:

$$C = \frac{\sum_{i=1}^{133} \Delta_i \Delta_i^T}{133} \qquad (4)$$

The principal components were obtained solving the following diagonalization problem:

$$Ce_k = \lambda_k e_k \qquad (5)$$

where $e_k$ is the k principal component and $\lambda_k$ is the eigenvalue of the k principal component. Considering $e_k$ as the k deformation pattern, more specifically as the k lens deformation pattern, the full shape of a crystalline lens can be represented as the average lens 3 plus a linear combination of the lens deformation patterns $e_k$:

$$l_i = \bar{l} + \sum_{k=1}^{K} a_k e_k \qquad (6)$$

where K is the number, at least one, of lens deformation patterns used in the representation $l_i$ of a full shape of a crystalline lens; $a_k$ is the scalar weight coefficient of the lens deformation pattern $e_k$. This implies that a given crystalline lens can be defined by at least one coefficient $a_k$, wherein k=1, . . . , K. Therefore, an advantage is that a full shape of a crystalline lens can be represented with a reduced amount of data, since the scalar weight coefficients $a_k$ are enough to characterize the full shape of the crystalline lens.

Formula (6) shows that a second plurality of points $l_i$ which are the estimated points of a full shape of a crystalline lens can be obtained by displacing a first plurality of points $\bar{l}$ following a plurality of directions and a plurality of lengths in said directions, wherein the plurality of directions and the plurality of lengths are given by the at least one lens deformation pattern $e_k$ in combination with the scalar weight coefficient $a_k$ of said lens deformation pattern $e_k$. Therefore, an advantage is that, unlike other methods of estimating full shapes of a crystalline lens from measurements taken in-vivo by optical imaging techniques, in the present method, once the lens deformation patterns $e_k$ have been obtained, the final result is a smooth and very compact model. The model is compact because it can be defined with a small number of weight coefficients $a_k$. The represented full shape of a lens is smooth because the lens deformation patterns are summed to the average lens 3, which is smooth by itself, leading to smooth full shape lenses.

In addition, each lens deformation pattern $e_k$ comprises a set of proportions between the length of displacement of a point of the average lens 3 and the length of displacement of the rest of the points of the average lens 3.

In addition, this estimation of a full shape of a lens based on lens deformation patterns $e_k$ allows easily shaping a 3-D digital model of a full shape of a lens because, since the lens deformation patterns $e_k$ are principal components and hence orthogonal to each of the rest of the lens deformation patterns $e_k$, a variation in the 3-D digital model of a full shape of a crystalline lens can be easily attributed to a small number of the lens deformation patterns $e_k$. Furthermore, the lens deformation patterns are easy to interpret and represent the joint variation of the geometry of the full shape of the crystalline lens (e.g., the anterior and posterior surfaces and the lens thickness), making easier the interpretation of the geometrical changes of the crystalline lens with age, accommodation or refraction for example.

The principal components (i.e. the lens deformation patterns $e_k$) having highest eigenvalues represent the main ways, or modes of variation, in which the points of a full shape of a lens tend to move together (i.e., represent how the full shape varies), across full shapes of lenses, with respect to the average lens 3. That is why the principal components can be considered lens deformation patterns.

The lens deformation patterns $e_k$ (i.e. principal components) which eigenvalues $\lambda_k$ are higher explain more variance across lenses than the lens deformation patterns $e_k$ which eigenvalues are lower. Thus, the lens deformation patterns $e_k$ with the highest eigenvalues $\lambda_k$ are the most significant modes of variation of the full shapes of lenses. An advantage of this is that very accurate representations can be obtained with a small number of lens deformation patterns $e_k$. For example, very accurate representations can be obtained with five or six lens deformation patterns $e_k$, although accurate representations can also be obtained with just two lens deformation patterns $e_k$. In addition, the lens deformation patterns $e_k$ are orthogonal to each of the rest of the lens deformation patterns $e_k$, being orthogonality a suitable feature of a basis representation, as it allows easy decoupling of the different lens deformation patterns.

Each of FIGS. 6A1 to 6F2 shows changes of an average lens 61 which are produced by two values, namely a positive value and a negative value, of the scalar weight coefficient $a_k$ of a particular lens deformation pattern $e_k$ according to the following equation:

$$l = \bar{l} + a_k e_k \qquad (7)$$

The two values for each scalar weight coefficient are $a_k = -3\sigma_k$ and $a_k = 3\sigma_k$, where $\sigma_k$ is the standard deviation of the coefficients over all the lenses for the eigenlens k. Note that a value of $a_k = 0$ in FIGS. 6A1 to 6F2 corresponds to the average lens 61, since in FIGS. 6A1 to 6F2, equation (7) has been used.

Figure 8:
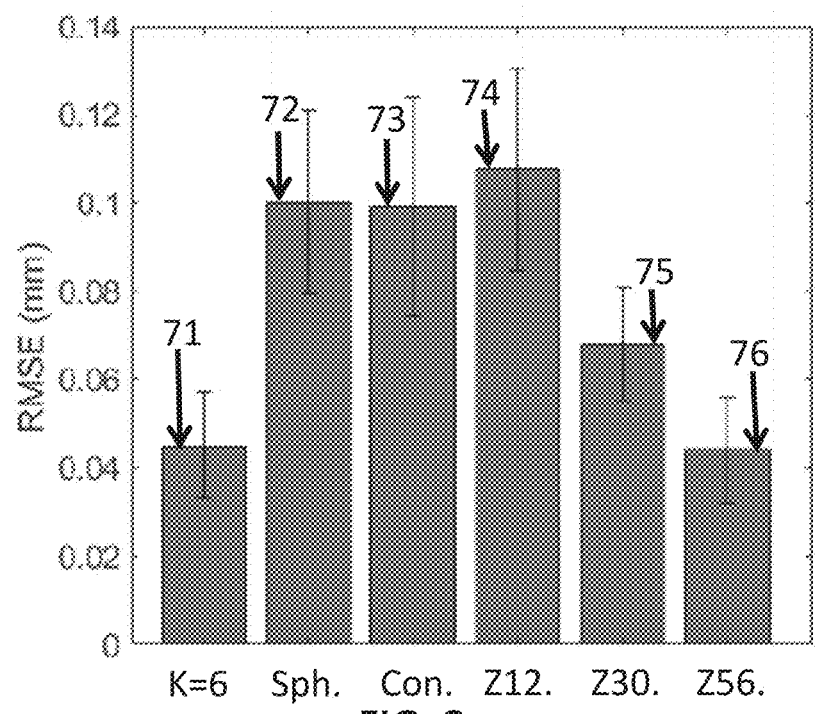

The lens deformation pattern $e_k$ of FIGS. 6A1 to 6A8 has the highest eigenvalue $\lambda_k$ of all the lens deformation patterns $e_k$ and hence is the most significant and the most common lens deformation pattern $e_k$ of the full shape of a crystalline lens across crystalline lenses. As shown in FIGS. 6A1 to 6A8 this lens deformation pattern $e_k$ changes the size of the full shape 61 of the lens. More specifically, the lens deformation pattern $e_k$ of FIGS. 6A1 to 6A8 generates an expansion of all the points of the full shape of the lens or a contraction of all the points of the full shape of the lens. The type of deformation (i.e. contraction of all the points of the full shape of a lens or expansion of all the points of the full shape of the lens) can be changed by changing the sign of the weight coefficient $a_k$, in the case shown in FIGS. 6A1 to 6A8 the contraction generated by applying a weight coefficient $a_k$ having a positive value.

An exemplary full shape 612 of the lens is generated by applying a scalar weight coefficient of $a_k = -3\sigma_k = -48.5$ to the lens deformation pattern $e_k$ of FIGS. 6A1 to 6A8 and adding the result to the average lens 61. An exemplary full shape 611 of the lens is generated by means of applying a scalar weight coefficient of $a_k = 3\sigma_k = 48.5$ to the lens deformation pattern $e_k$ of FIGS. 6A1 to 6A8 and adding the result to the average lens 61.

The lens deformation pattern $e_k$ of FIGS. 6A1 to 6A8 has been represented alone, that is without being added to any average lens 3, in FIGS. 5A1 and 5A2.

The lens deformation pattern $e_k$ of FIGS. 6B1 to 6B8 has the second highest eigenvalue $\lambda_k$ of all the lens deformation patterns illustrated in FIGS. 6A1 to 6F2. As shown in FIGS. 6B1 to 6B8 this lens deformation pattern changes the aspect ratio of the full shape 61 of the lens, that is, the lens deformation pattern flattens the anterior and posterior portion of the full shape of the lens and at the same time increases the equatorial diameter and decreases the central lens thickness of the full shape of the lens.

An exemplary more flattened full shape 622 of a lens is generated by applying a scalar weight coefficient of $a_k = -3\sigma_k = -33.1$ to the lens deformation pattern $e_k$ of FIGS. 6B1 to 6B8. An exemplary less flattened full shape 621 of the lens is generated by applying a scalar weight coefficient of $a_k = 3\sigma_k = 33.1$ to the lens deformation pattern $e_k$ of FIGS. 6B1 to 6B8.

The lens deformation pattern $e_k$ of FIGS. 6B1 to 6B8 has been represented alone, that is without being added to any average lens 3, in FIGS. 5B1 and 5B2.

The lens deformation pattern $e_k$ of FIGS. 6C1 to 6C3 and the lens deformation pattern $e_k$ of FIGS. 6D1 to 6D2 have the third and fourth highest eigenvalues $\lambda_k$ respectively. As shown in FIGS. 6C1 to 6C3 and 6D1 to 6D2 each of these lens deformation patterns $e_k$ asymmetrically changes the full shape 61 of the average lens.

The lens deformation pattern $e_k$ of FIGS. 6C1 to 6C3 has been represented alone, that is without being added to any average lens 3, in FIGS. 5C1 and 5C2. The lens deformation pattern $e_k$ of FIGS. 6D1 to 6D2 has been represented alone, that is without being added to any average lens 3, in FIGS. 5D1 and 5D2.

The lens deformation pattern $e_k$ of FIGS. 6E1 to 6E3 and the lens deformation pattern $e_k$ of FIGS. 6F1 to 6F3 have the fifth and sixth highest eigenvalues $\lambda_k$ respectively. As shown in FIGS. 6E1 to 6E3 and 6F1 to 6F3 each of these lens deformation patterns $e_k$ finely changes the full shape 61 of the average lens. These changes are related with the asphericity of conicoids or with rotationally symmetric Zernike polynomials.

The lens deformation pattern $e_k$ of FIGS. 6E1 to 6E3 has been represented alone, that is without being added to any average lens 3, in FIGS. 5E1 and 5E2.

Therefore, a full shape of a lens can be defined accurately with just a few lens deformation patterns $e_k$, preferably with the lens deformation patterns $e_k$ having the highest eigenvalues $\lambda_k$, plus the average lens 61. The higher the number of scalar weight coefficients $a_k$ used, the higher the accuracy and precision of the estimated full shape are, but more calculations and data memory are required, and a less compact representation is obtained.

Furthermore, since each lens deformation pattern $e_k$ is orthogonal to the rest of the lens deformation patterns $e_k$, each lens deformation pattern $e_k$ is not correlated with any of the rest lens deformation patterns $e_k$ and thus any lens estimated from a set of scalar weight coefficients $\{a_k\}$ within the range of values of the training set is realistic. That is, to obtain a realistic lens is advantageous that the value of each scalar weight coefficient $a_k$ is within a range of values having a maximum which is the highest value of said scalar weight coefficient for any lens of the 133 lenses and a minimum which is the lowest value of said scalar weight coefficient $a_k$ for any lens of the 133 lenses. As explained above, the 133 crystalline lenses have been ex-vivo measured and from these measurements the full shape of the average lens 3, 61 and the lens deformation patterns $e_k$ have been obtained following the previous steps 1 to 6.

In order to evaluate the accuracy of a full shape estimated from lens deformation patterns $e_k$ and an average lens 3, 61, and hence in order to evaluate the capability of representing the full shape of a lens which is different from the 133 lenses, 10-fold cross validation was performed, i.e., the training set consisted of N=120 of the 133 lenses and the test set consisted of the remaining 13 of the 133 lenses, shifting the test set in each fold. In the test step of the 10-fold cross validation the scalar weight coefficients $a_k$ of each particular crystalline lens of the test set were estimated by subtracting the average lens 1 from the 3-D digital model of the full shape of a particular crystalline lens, obtaining as a result the residual data $\Delta_n$ of the particular crystalline lens. Thereafter, the residual data $\Delta_n$ were projected into the lens deformation patterns $e_k$ obtained with the train set (i.e. projected into the principal components).

The 10-fold cross validation was repeated 100 times, and root mean squared error (RMSE) was estimated averaging the error in the test sets. The error being the difference between an actual full shape of the lens of the test set and its estimation with a number of K lens deformation patterns $e_k$.

In order to understand the influence of a variation in the number K of lens deformation patterns $e_k$ in the representation of a full shape of a lens, two metrics were analysed: percentage of variance (PVar) explained by the set of the first K eigenlenses; and root mean squared error (RMSE) obtained by applying the 10-fold cross validation as explained above. Standard deviation (STD) of the RMSE (across lenses and folds) and of the PVar (across folds) was also calculated. Note that if PVar=100 or RMSE=0 the full shape of all the test lenses can be represented without error.

FIG. 7 shows the STD and the arithmetic mean of PVar and STD and the arithmetic mean of RMSE as a function of the number of lens deformation patterns K used to represent a full shape of a lens. The value of the arithmetic mean of the RMSE is represented with points 910-919 and the value of the STD of the RMSE is represented by means of error bars centered in the arithmetic mean of the RMSE, wherein the total length of each error bar is of 2 STD. The value of the arithmetic mean of the PVAR is represented with a dashed line 920 and the value of the STD of the PVAR is represented by means of error bars centered in the arithmetic mean of the PVAR, wherein the total length of each error bar is of 2 STD.

In the light of the values of the mean of RMSE and the mean of Pvar, it can be considered that the method of estimating full shapes of lenses using lens deformation patterns $e_k$ and an average full shape of a lens 3, 61 is accurate. In addition, in the light of the graph shown in FIG. 7, K=6 could be considered as the optimal number of lens deformation patterns $e_k$ because, as it can be seen in the graph, higher values of K do not significantly decrease the RMSE (or do not significantly increase the PVar).

In order to assess if the accuracy achieved by state-of-the-art (SoA) methods of representation of full shapes of lenses were significantly different (statistical significance was defined as a p-value lower than 0.05) from an estimation of a full shape of a lens using K=6 lens deformation patterns, RMSE averaged across the test lenses was compared by applying multiple comparison test with the Bonferroni correction. The arithmetic mean and standard deviation of the RMSE of the following SoA representation methods was estimated:

Full shapes of lenses estimated by obtaining the best sphere fitting of the anterior portion of the full shape, the posterior portion of the full shape, the lens thickness and the position of the apex of the posterior surface of the full shape, hence using in total five parameters since the position of the apex is given by two parameters.

Full shapes of lenses estimated by obtaining the best conicoid fittings, that comprised the same parameters as the best sphere fitting of the previous SoA method (the anterior surface of the full shape, the posterior surface of the full shape, the lens thickness and the position of the apex of the posterior surface of the full shape) plus asphericity values of the anterior surface of the full shape and the posterior surface of the full shape, hence using in total seven parameters.

Zernike approximation of the anterior surface and the posterior surface of a full shape of a lens, using 6, 15 and 28 coefficients for estimating the anterior surface of the full shape and 6, 15 and 28 coefficients respectively for estimating the posterior full shape. In total 12, 30 and 56 coefficients respectively).

FIG. 8 shows rectangular bars which height correspond to a mean of the RMSE value estimated for a representation method of a full shape of a lens. The mean 71 of the RMSE with K=6 lens deformation patterns was significantly lower than the mean 72 of the RMSE with sphere fitting SPh., significantly lower than the mean 73 of the RMSE of the conicoid fitting Con., significantly lower than the mean 74 of the Zernike approximation using 12 coefficients Z12. and significantly lower than the mean 75 of the Zernike approximation using 30 coefficients Z30, while using a similar number of parameters (i.e. six parameters) when compared to sphere fitting (five parameters) and conicoid fitting (seven parameters), and a lower number of parameters than the Zernike approximations Z12. and Z30. Only the Z56. representation obtained a similar mean 76 of the RMSE, but requiring many more parameters (56 parameters instead of 6).

The mean value 72 of RMSE of the best sphere fitting Sph. was 2.23 times the mean value 71 of the RMSE for K=6 lens deformation patterns. The mean value 73 of RMSE of the best conicoid fitting Con. was 2.20 times the mean value 71 of the RMSE for K=6 lens deformation patterns. The mean value 74 of RMSE of the Zernike approximation of 12 coefficients Z12. was 2.39 times the mean value 71 of the RMSE for K=6 lens deformation patterns. The mean value 74 of RMSE of the Zernike approximation of 30 coefficients Z30. was 1.51 times the mean value 71 of the RMSE for K=6 lens deformation patterns.

Figure 9:
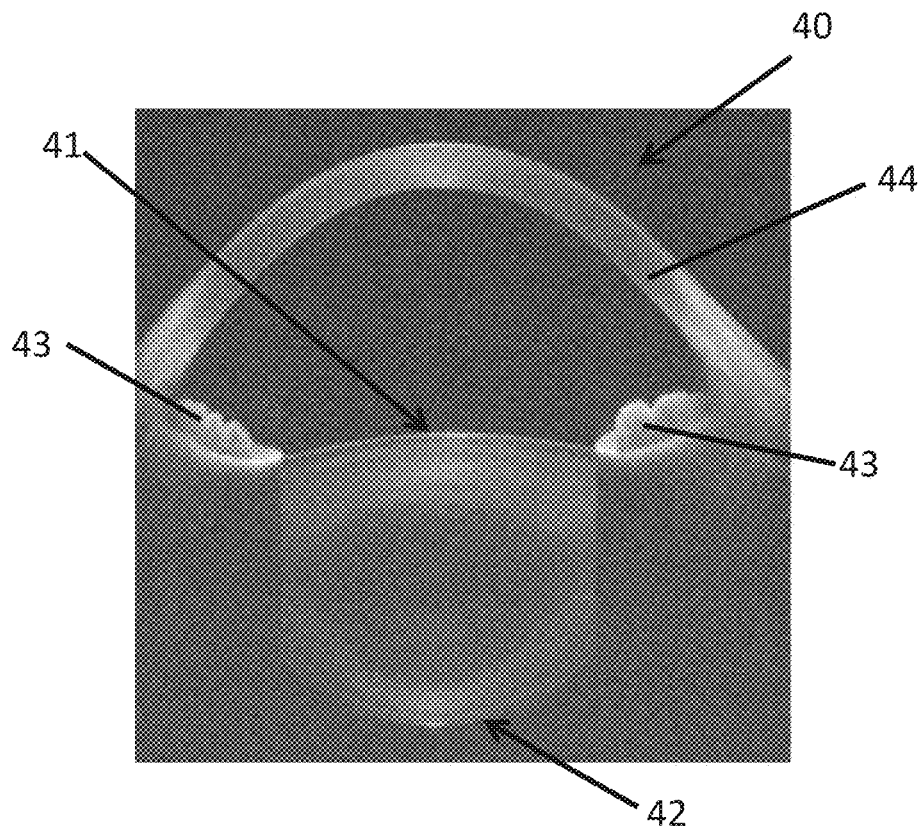
FIG. 9 shows an image of a cross-section of an anterior segment of an eye, wherein the image has been obtained from measurements taken in-vivo by an OCT (Optical Coherence Tomography) technique.

In order to obtain the at least one scalar weight coefficient $a_k$ of the estimated full shape of an in-vivo particular crystalline lens, measurements of the crystalline lens are required. As explained in the STATE OF THE ART and in the DESCRIPTION OF THE INVENTION, optical imaging techniques may be used to obtain the measurements. FIG. 9 shows an image of an anterior segment 40 of an eye wherein the image has been obtained by OCT performed in-vivo. FIG. 9 shows a cornea 44, an anterior surface 41 of a crystalline lens of an eye and a posterior surface 42 of the crystalline lens. Optical imaging techniques performed in-vivo do not allow measuring portions of the full shape of the crystalline lens which are not visible through the pupil of an eye. These non-visible portions of the crystalline lens cannot be measured with an optical imaging technique performed in-vivo because the iris 43 blocks the light from the optical device used in the optical imaging technique. Therefore, just a central part of the anterior portion 41 of the lens and a central part of the posterior portion 42 of the lens can be measured with an optical imaging technique.

Figures 10A, 10B:
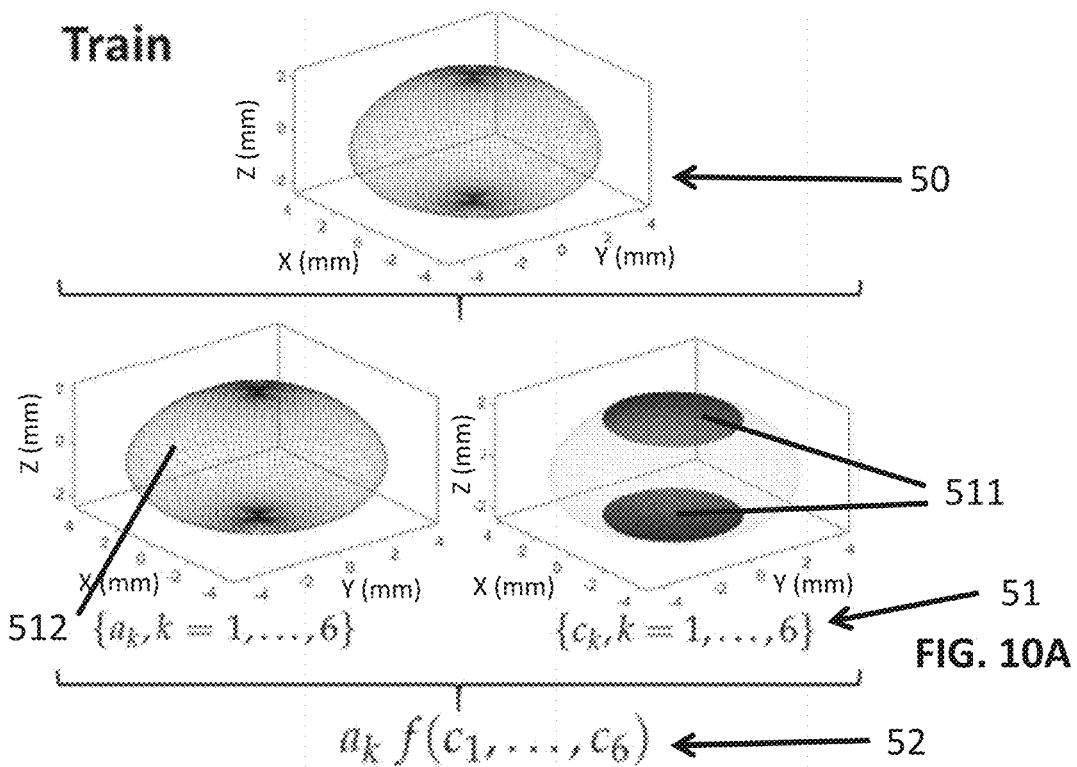
FIG. 10A schematically illustrates an obtention of parametric expressions for estimating weight coefficients of full shape lens deformation patterns from weight coefficients of deformation patterns of an anterior and posterior portion of the full shape of the crystalline lens.
FIG. 10B schematically illustrates the estimation of a full shape of a crystalline lens from an estimation of an anterior and posterior portion of the full shape of the crystalline lens.

The suitability of the lens deformation patterns $e_k$ in the estimation of full shapes of lenses under these disadvantageous conditions, in which just part of the anterior portion and part of the posterior portion of the lens may be measured, was evaluated by simulating the in-vivo conditions of measurement. In this way, an experiment was performed in which ex-vivo measurements of the crystalline lenses were restricted to a central part of the anterior portion of the lens and a central part of the posterior portion of the lens. Part of the experiment is schematically shown in FIGS. 10A and 10B.

In the experiment, the measurements of the crystalline lens were restricted to the central part of the anterior portion and the central part of the posterior portion of the lens which would result visible through a pupil of 5 mm of diameter. Thereafter the experiment was repeated restricting the measurements to the central part of the anterior portion and the central part of the posterior portion of the lens which would result visible through a pupil of 4 mm of diameter. In order to estimate the at least one scalar weight coefficient $a_k$ of the lens deformation patterns $e_k$ from these measurements of the lens simulating the in-vivo conditions, the following methodology was followed.

First of all, deformation patterns of an anterior and a posterior portion of the full shape of a lens were determined from the 133 crystalline lenses. These deformation patterns, unlike the lens deformation patterns $e_k$, merely define the deformation of an anterior and a posterior portion 511 of the full shape of a lens and not the deformation of the full shape of the lens.

The deformation patterns of an anterior and a posterior portion of the full shape were obtained in a similar way as the lens deformation patterns $e_k$ were obtained in previous steps 1 to 6 with the following differences:

In steps 1 to 4, the 3-D digital model is not a 3-D digital model of the full shape of a lens but a 3-D digital model of the anterior and posterior portion 511 of a full shape of a lens. Therefore, in step 4 it was not obtained the positions of the points defining a full shape of a lens but the positions of the points defining merely the anterior and posterior portions 511 of the full shape of a lens.

In step 5, instead of obtaining an average 3, 61 $\bar{l}$ of the full shape of a crystalline lens, it was obtained an average of merely the anterior and posterior portion 511 the full shape of a crystalline lens. In addition, instead of obtaining the residual data $\Delta_n$ of a full shape of a crystalline lens it was obtained the residual data of merely the anterior and posterior portion 511 the full shape of a crystalline lens.

In step 6, instead of obtaining the covariance matrix C of the residual data of full shapes of crystalline lenses, it was obtained the covariance matrix of merely the anterior and posterior portion 511 of a full shape of a crystalline lens. In addition, instead of obtaining the principal components $e_k$ of a full shape of a lens, it was obtained the principal components of merely the anterior and posterior portion 511 of the full shape of a lens. Therefore, the anterior and posterior portions 511 of a full shape of a lens can be defined by scalar weight coefficients $c_k$ of the deformation patterns of an anterior and posterior portions in the same manner as a full shape of a crystalline lens can be defined by scalar weight coefficients $a_k$ of the lens deformation patterns $e_k$.

For the sake of conciseness, hereinafter, a scalar weight coefficient of the deformation patterns of an anterior and a posterior portion of a full shape of a lens is called "secondary weight coefficient" in order to distinguish this coefficient from a scalar weight coefficient $a_k$ of a lens deformation pattern $e_k$.

Thereafter, it was calculated a set of parametric expressions, which are shown in equations (8), for estimating the scalar weight coefficients $a_k$ of each lens deformation pattern $e_k$ from the secondary coefficients $c_k$ of the same full shape of a lens. This set of parametric expressions (8) were obtained from the application of multiple linear regression using least squares to the 133 lenses:

$$a_1 = f_1(c_1, \ldots, c_6)$$

$$a_2 = f_2(c_1, \ldots, c_6)$$

$$a_3 = f_3(c_1, \ldots, c_6)$$

$$a_4 = f_4(c_1, \ldots, c_6)$$

$$a_5 = f_5(c_1, \ldots, c_6)$$

$$a_6 = f_6(c_1, \ldots, c_6) \quad (8)$$

In this manner, the full shape of a crystalline lens can be estimated from the anterior and posterior portions of a full shape of a crystalline lens. The reason is that the weight coefficients $a_k$ of the lens deformation patterns $e_k$ may be estimated from the secondary weight coefficients $c_k$ by using the set of parametric expressions (8). Therefore, since the measurements of just the anterior and posterior portion 511 of a full shape of a lens allow estimating the secondary weight coefficients $c_k$, the full shape of a crystalline lens may be estimated from measurements of just the anterior and posterior portions 511 of said crystalline lens. In order to evaluate the goodness of the fit of this way of estimation of a full shape of a lens from measurements of just the anterior and posterior portions, the following experiment, which is illustrated in FIGS. 10A and 10B, was performed.

First of all, the 133 crystalline lenses were divided in a training set of 120 crystalline lenses and a test set of 13 crystalline lenses. The full shape 512 of each lens of the training set and anterior and posterior portions 511 of each lens of the training set were measured in order to calculate the set of parametric expressions 52 which give weight coefficients $a_k$ of a lens as a function of secondary weight coefficients $c_k$ of said lens, as schematically shown in FIG. 10A. Thereafter, the test lenses were measured simulating in-vivo conditions and hence restricting the measurements to a central part of the anterior and posterior portions 53 (i.e. simulating a pupil of 5 mm of diameter or a pupil of a pupil of 4 mm of diameter), calculating the secondary weight coefficients $c_k$ of the measured lens. Then, as schematically shown in FIG. 10B, the set of parametric expressions 52 was applied to estimate the weight coefficients $a_k$ from the secondary weight coefficients $c_k$ and hence estimating the full shape 55 of lens from the test set.

The difference between the estimated full shapes of the test lenses and the actual full shape of the test lenses was used to estimate the accuracy of this method of estimating a full shape of a lens.

Table 1 illustrates the goodness of the estimation of the full shape from the central part. The goodness was evaluated by means of calculating the adjusted coefficient of determination $R^2$ and the p-value for the prediction of the scalar weight coefficients $a_k$ of the lens deformation patterns $e_k$ from the secondary weight coefficients $c_k$.

TABLE 1

| Predicted $a_k$ | $R^2$ 4 mm | $R^2$ 5 mm | p-value 4 mm | p-value 5 mm |
| --- | --- | --- | --- | --- |
| $a_1$ | 0.94 | 0.05 | $10^{-76}$ | $10^{-76}$ |
| $a_2$ | 0.93 | 0.94 | $10^{-72}$ | $10^{-76}$ |

TABLE 1-continued

| Predicted $a_k$ | $R^2$ 4 mm | $R^2$ 5 mm | p-value 4 mm | p-value 5 mm |
| --- | --- | --- | --- | --- |
| $a_3$ | 0.84 | 0.86 | $10^{-49}$ | $10^{-51}$ |
| $a_4$ | 0.87 | 0.88 | $10^{-55}$ | $10^{-57}$ |
| $a_5$ | 0.53 | 0.73 | $10^{-25}$ | $10^{-33}$ |
| $a_6$ | 0.13 | 0.07 | 0.006 | 0.16 |

In addition, the accuracy of the of the estimated full shapes was evaluated by means of calculating the average RMSE between the actual full shape of a lens and the full shape estimated with the estimated scalar weight coefficients $a_k$ of the lens deformation patterns $e_k$. The average RMSE in the experiment simulating a pupil of 4 mm of diameter was of RMSE=0.072±0.023. The average RMSE in the experiment simulating a pupil of 5 mm of diameter was of RMSE=0.068±0.022.

Thereby, the full shape of a crystalline lens in-vivo measured with optical imaging techniques can be estimated by obtaining the estimated scalar weight coefficients $a_k$ achieving a high accuracy in the estimation of the full shape. Therefore, this method of estimation of a full shape of a lens is advantageous in the customization of solutions for cataracts and presbyopia. For example, it is advantageous for estimating the position of an IOL implantable in the eye. In addition, it is potentially advantageous for prospective surgical techniques for counteracting the effects of presbyopia. Some examples of these techniques are those surgical techniques based on lens refilling or those for sizing accommodative IOLs which design largely depends on the volume of the capsular bag and the equatorial diameter of the crystalline lens. A reason why this method of estimation of a full shape of a crystalline lens is advantageous for sizing these accommodative IOLs is that the volume of the capsular bag and the equatorial diameter of the lens can be estimated from the estimated full shape. For example, some accommodative IOL comprise one or two components, which axial positions depend on lens size. In addition, this method of estimation of a full shape of a crystalline lens is advantageous in some accommodative IOLs which encompass mechanisms to reshape that rely on the squeezing or relaxation of the capsular bag. In these accommodative IOLs, the fluid released from the reservoir located in, for example, the haptics may flow into the central portion of the lens reshaping the lens. The reshaping of the central portion of the lens is affected by the capsular bag; the method of estimating a full shape of a crystalline lens allows improving the estimation of the shape of the capsular bag and hence the estimation of the reshaping.

In addition, the high accuracy and precision achieved in the estimation of the full shape of a lens allows designing an IOL which is more appropriate for a particular eye, improving customization of the IOLs.

In addition, the high accuracy and precision achieved in the estimation of the full shape of a lens facilitate studying the changes undergone by the full shape of a crystalline lens due to in-vivo aging, particularly during infancy and childhood.

Another advantage is that, in order to achieve high accuracy, a low number of scalar weight coefficient $a_k$ is needed.

Some embodiments of the method according to the present invention can be applied to generate random realistic full shapes of a lens of an eye by assigning random values to the scalar weight coefficients $a_k$ of the lens deformation patterns $e_k$. For example, it can be applied to random generation of a realistic full shapes of a crystalline lens of an eye of a person who is of a particular age, as described below.

The underlying conditional probability distribution of the scalar weight coefficients $a_k$ given a particular age $P(a_1, \ldots, a_K|age=A)$ was estimated. It was assumed that the probability distribution $P(a_1, \ldots, a_K|age=A)$ was a multivariate normal distribution, and the mean vector and the covariance matrix of the probability distribution $P(a_1, \ldots, a_K|age=A)$ were estimated.

In order to avoid the restriction of using data of only the crystalline lenses of a specific age in order to estimate the mean vector and the covariance matrix for that age, all the data (i.e. the data of the full shape of the 133 lenses) were used, weighing every sample using a Gaussian kernel $$e^{-\frac{1}{W}*(age_{sample}-A)^2},$$

which depends on the square difference between the age of interest A and the age of each specific sample $age_{sample}$. The parameter W, which controls the width of the Gaussian kernel, was set to 5. The covariance matrix and the mean vector were estimated from the weighed data.

Once the probability distribution had been estimated, crystalline lenses of a given age A could be generated by means of sampling from the probability distribution $P(a_1, \ldots, a_K|age=A)$, obtaining for example typical full shapes of crystalline lenses, such as the one corresponding to the mean vector of the probability distribution, "atypical" full shapes of crystalline lenses, i.e. those which values of the scalar weight coefficients $a_k$ are far away from the mean vector, or random lenses by randomly sampling the distributions.

Figure 11A:
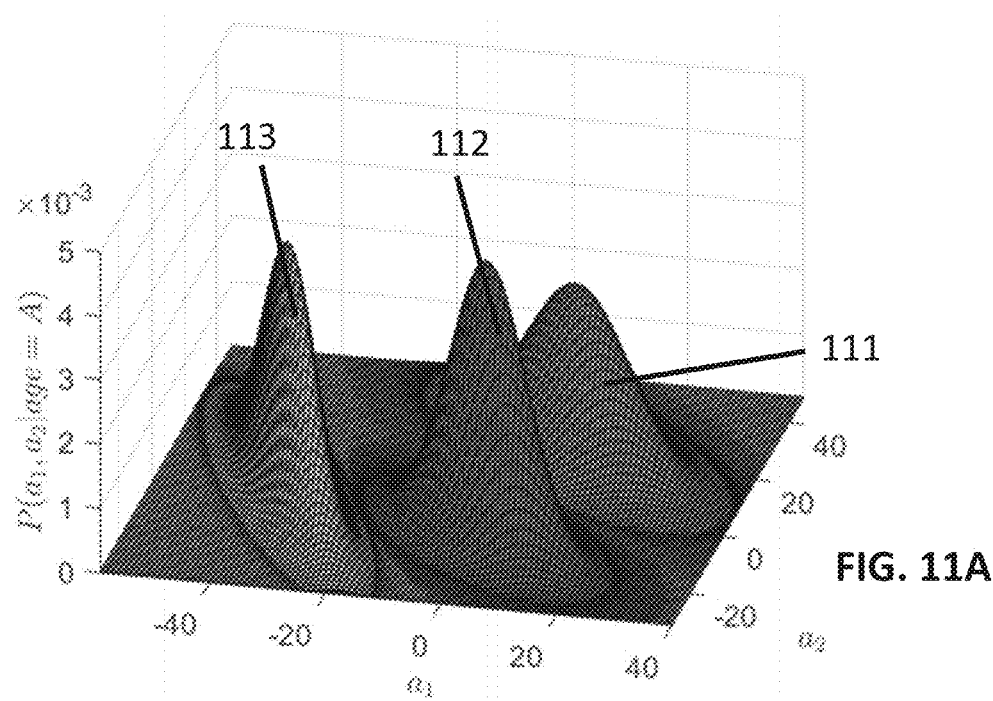
FIG. 11A shows three different two-dimensional probability distributions of two weight coefficients of lens deformation patterns, wherein each probability distribution is a conditional probability distribution wherein the condition is that the crystalline lens is of a particular age.
Figure 11B:
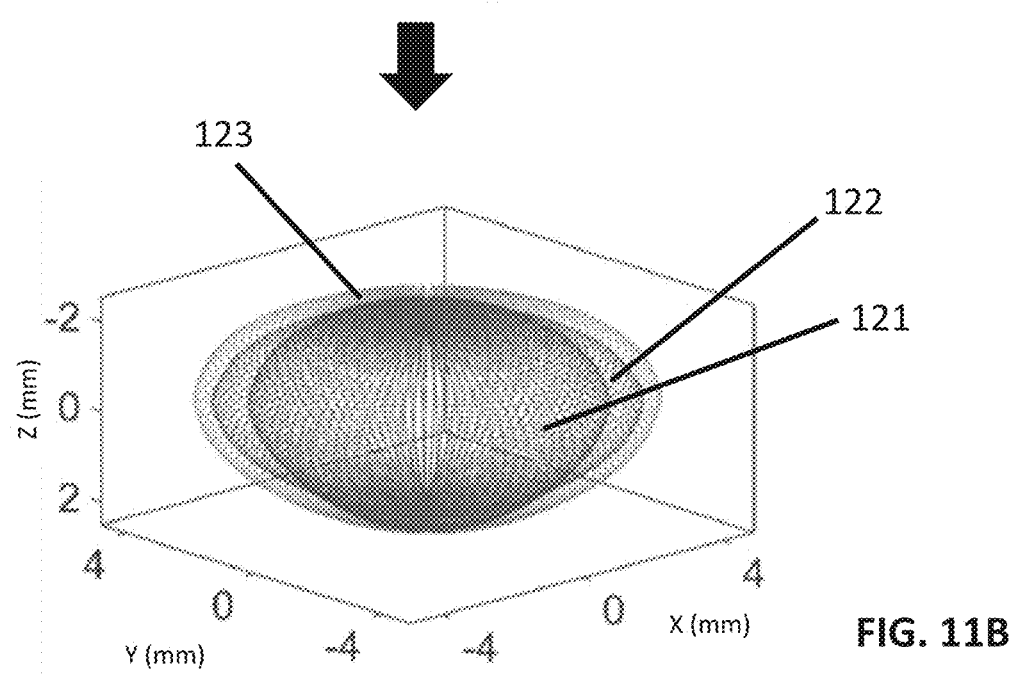
FIG. 11B shows full shapes of crystalline lenses randomly generated by means of sampling the probability distributions shown in FIG. 11A.

FIG. 11A shows the probability distribution $P(a_1, \ldots, a_K|age=A)$ with two scalar weight coefficients $a_k$ for three ages: $P(a_1, a_2|age=60 \text{ y/o})$ 113, $P(a_1, a_2|age=30 \text{ y/o})$ 112 and $P(a_1, a_2|age=5 \text{ y/o})$ 111. From each distribution, a random vector $(a_1, a_2)$ was obtained. FIG. 11B shows the full shape of the crystalline lenses generated with the obtained vectors $(a_1, a_2)$. The vector $(a_1, a_2)$ of the full shape 121 of a crystalline lens of 5 y/o was generated from the probability distribution $P(a_1, a_2|age=5)$ 111. The vector $(a_1, a_2)$ of the full shape 122 of a crystalline lens of 30 y/o was generated from the probability distribution $P(a_1, a_2|age=30)$ 112. The vector $(a_1, a_2)$ of the full shape 123 of a crystalline lens of 60 y/o was generated from the probability distribution $P(a_1, a_2|age=60)$ 113.

Thereby, realistic full shapes of crystalline lenses of an eye of a particular age A can be generated by means of sampling the probability distribution $P(a_1, \ldots, a_K|age=A)$ corresponding to the age A. Therefore, advantageously, the changes to which a full shape of a lens is subjected due to aging can be easily inferred from the probability distributions $P(a_1, \ldots, a_K|age=A)$. For example, this facilitates the study of potential implications of changes of a full shape of a crystalline lens in the development of refractive errors.

In addition, automatic construction of realistic lenses is important for building computational models of crystalline lens accommodation representative of a large population and to virtually test the effects of treatment or IOL implantation prior to studies in vivo (or even ex vivo).

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the present disclosure is obviously not limited to the specific embodiment(s) described herein, but also encompasses any variations that may be considered by any person skilled in the art (for example, as regards the choice of materials, dimensions, components, configuration, etc.), within the general scope thereof as defined in the claims.

What is claimed is:

1. Method of estimating a full shape of a lens from measurements of the lens taken in-vivo by optical imaging techniques, the measurements comprising visible portions of the lens, the method comprises defining non-visible portions of the lens parting from the in-vivo measurements and using a geometrical model of a lens previously built from ex-vivo measurements, the method comprising the steps of:
   receiving, by a data-processing system, the in-vivo measurements of the lens;
   determining, by the data-processing system, non-visible portions of the lens parting from the in-vivo measurements, the method characterized in that the step of determining non-visible portions of the lens comprises:
   a) establishing a location of a first plurality of points which defines an initial full shape of a crystalline lens; and
   b) displacing the first plurality of points a plurality of lengths following a plurality of directions to a location of a second plurality of points, wherein the second plurality of points are estimated points of the full shape of the lens of which the in-vivo measurements have been taken, wherein the initial full shape of a crystalline lens is obtained from ex-vivo measurements, and the plurality of lengths is estimated from the in-vivo measurements.

2. The method of claim 1, wherein displacing the first plurality of points a plurality of lengths following a plurality of directions to a location of a second plurality of points comprises displacing according to at least one lens deformation pattern, wherein the at least one lens deformation pattern is obtained from ex-vivo measurements.

3. The method of claim 2, wherein each lens deformation pattern defines a ratio for each pair of points which are displaced according to the lens deformation pattern, each ratio being a ratio between a length of displacement of a point of the pair of points and a length of displacement of the other point of the pair of points.

4. The method of claim 2, wherein the plurality of lengths of step b) are obtained by applying a weight coefficient to each of the at least one lens deformation pattern, wherein the at least one weight coefficient is estimated from the in-vivo measurements.

5. The method of claim 4, wherein the step of displacing the first plurality of points (3, 61) is performed according to the equation:

$$l = l_0 + \sum_{k}^{K} a_k e_k$$

where:
l is a matrix which contains coordinates of the second plurality of points (55) resulting from displacing the first plurality of points (3, 61);
$l_0$ is a matrix which contains coordinates of the first plurality of points (3, 61);

$e_k$ is a matrix which defines a k lens deformation pattern (811, 821, 831, 841, 851) of the at least one lens deformation pattern, the $e_k$ matrix defining displacements of the first plurality of points (55);

$a_k$ is a k scalar weight coefficient of the at least one weight coefficient;

K is a total number of lens deformation patterns (811, 821, 831, 841, 851) used to estimate the full shape of the lens.

6. The method of claim 4, wherein each weight coefficient applied to each lens deformation pattern is estimated from at least one secondary coefficient wherein each of the at least one secondary coefficient is a coefficient applied to a deformation pattern of a central anterior portion and of a central posterior portion of a full shape of a crystalline lens, the method comprising the step of:

calculating the at least one secondary coefficient applied to a deformation pattern of a central anterior portion and of a central posterior portion of a full shape of a crystalline lens; wherein the at least one deformation pattern of a central anterior portion and of a central posterior portion is obtained from ex-vivo measurements; and wherein the at least one secondary coefficient is calculated from the in-vivo measurements.

7. The method of claim 4, the method further comprising estimating the at least one weight coefficient as a function of estimated geometric parameters of the lens measured in-vivo, the estimated geometric parameters being estimated from the in-vivo measurements, and the geometric parameters being characteristic geometric parameters of a shape of a lens such as lens thickness, radius of curvature of an anterior surface of the lens, radius of curvature of a posterior surface of the lens or Zernike coefficients describing surfaces of the lens.

8. The method of claim 4, wherein a lens volume and/or a lens surface area and/or the lens diameter and/or the lens equatorial position are/is estimated as a function of the at least one weight coefficient.

9. The method of claim 2, wherein each lens deformation pattern is an eigenvector of a covariance matrix of residual data, wherein the residual data are a difference between a full shape of each lens of a set of ex-vivo lenses and an average full shape of the set of ex-vivo lenses.

10. A method of predicting an estimated lens position of a lens implantable in an eye, wherein the estimated lens position is obtained from the full shape of the in-vivo measured lens, the full shape of the in-vivo measured lens being estimated using a method according to claim 1.

11. The method of claim 10, wherein the estimated lens position of a lens implantable in an eye is obtained using the following formula:

$$ELP = C_0 + \sum_{k}^{K} a_k C_k$$

where:

ELP is the estimated lens position;

$a_k$ is a k scalar weight coefficient of the at least one weight coefficient;

$C_k$ is a k positioning weight coefficient;

$C_0$ is a bias term.

12. A method of selecting an intraocular lens implantable in an eye, which comprises using the method of claim 1 to calculate the estimated lens position of the intraocular lens.

13. A data-processing system, which comprises processing means for carrying out the method of claim 1.

14. A method of estimating a full shape of a crystalline lens from measurements of the lens taken by optical imaging techniques, the method comprises:

a) estimating at least one weight coefficient from the measurements;

b) applying a lens deformation pattern to each at least one weight coefficient to obtain a plurality of lengths of displacement, wherein the at least one lens deformation pattern is obtained from ex-vivo measurements;

c) displacing a first plurality of points the plurality of lengths of displacement obtained in step b) to a location of a second plurality of estimated points of the full shape of a lens.

15. A data-processing system configured to determine a full shape of a crystalline lens by means of displacing a first plurality of points a plurality of lengths following a plurality of directions to a location of a second plurality of points, wherein the first plurality of points defines an initial full shape of a crystalline lens, the initial full shape is obtained from ex-vivo measurements, and the plurality of lengths is obtained by applying a weight coefficient to each of at least one lens deformation pattern.

16. The data-processing system of claim 15 comprising processing means for generating a realistic full shape of a crystalline lens, wherein the realistic full shape of a crystalline lens is defined by assigning values to the at least one weight coefficient, wherein the value of each of the at least one weight coefficient is within a minimum and a maximum values obtained from the ex-vivo measurements.

17. The data-processing system of claim 16, wherein the values assigned to the at least one weight coefficient are randomly taken from a probability distribution selected from a number of predetermined probability distributions, wherein each probability distribution of the number of predetermined probability distributions is for a particular age range.

18. An optical imaging device comprising the data-processing system of claim 15.

* * * * *